(12) United States Patent
Fujiwara

(10) Patent No.: US 8,107,170 B2
(45) Date of Patent: Jan. 31, 2012

(54) OBJECTIVE OPTICAL SYSTEM

(75) Inventor: Masato Fujiwara, Tokyo (JP)

(73) Assignee: Olympus Corporation, Tokyo (JP)

( * ) Notice: Subject to any disclaimer, the term of this patent is extended or adjusted under 35 U.S.C. 154(b) by 57 days.

(21) Appl. No.: 12/619,119

(22) Filed: Nov. 16, 2009

(65) Prior Publication Data

US 2010/0123950 A1 May 20, 2010

(30) Foreign Application Priority Data

Nov. 19, 2008 (JP) ................................ 2008-295713
Sep. 25, 2009 (JP) ................................ 2009-221390

(51) Int. Cl.
*G02B 21/02* (2006.01)
(52) U.S. Cl. ................ 359/659; 359/656; 359/362
(58) Field of Classification Search .............. 359/362, 359/368, 656–661
See application file for complete search history.

(56) References Cited

U.S. PATENT DOCUMENTS

| 5,502,596 A * | 3/1996 | Suzuki ........................... 359/657 |
| 7,215,478 B1 * | 5/2007 | Hirata ........................... 359/656 |
| 7,268,953 B2 * | 9/2007 | Matthae et al. ............... 359/656 |
| 7,304,789 B2 * | 12/2007 | Hirata et al. .................. 359/368 |

FOREIGN PATENT DOCUMENTS

JP  2006-119300  5/2006

* cited by examiner

*Primary Examiner* — Thong Nguyen
(74) *Attorney, Agent, or Firm* — Scully, Scott, Murphy & Presser, P.C.

(57) ABSTRACT

An objective optical system includes, in sequence from the object side, a first group having positive refractive power and including a plano-convex lens with the convex surface facing the image side; a second group having positive refractive power and including a lens whose extreme-object-side lens surface is convex facing the object side; a third group having negative refractive power and including a lens whose extreme-image-side lens surface is concave facing the image side; a fourth group having positive refractive power and including a lens disposed on the extreme object side, whose image-side lens surface is convex facing the image side and a lens disposed on the extreme image side, whose object-side lens surface is convex facing the object side; and a fifth group having positive refractive power and including a combined lens by joining a convex lens and a concave lens, the joined surface having negative refractive power.

11 Claims, 13 Drawing Sheets

OBJECTIVE OPTICAL SYSTEM

CROSS REFERENCE TO RELATED APPLICATIONS

This application claims benefit of Japanese Applications No. 2008-295713 filed in Japan on Nov. 19, 2008 and No. 2009-221390 filed in Japan on Sep. 25, 2009, the contents of each of which are hereby incorporated by their reference.

BACKGROUND OF THE INVENTION

1. Field of the Invention

The present invention relates to an objective optical system.

2. Description of Related Art

Conventionally, microscopic observation using an objective optical system is widely used. For example, in order to observe the behavior or the like of biological molecules in cells and tissue of cultured organisms using images, a method in which specific molecules, tissue, cells, or the like tagged with a colorant or fluorescent marker are observed with a fluorescence microscope, a confocal laser scanning microscope, or the like is known. In recent years, because the behavior of molecules of living mammal organisms, such as mice, is sometimes different from that of cultured cells, various in vivo imaging techniques, which enable observation of biological molecules in the living tissue and cells while the living organism is alive (in vivo), have been proposed. Furthermore, in order to observe a living organism in a minimally invasive manner, there has been proposed a microscope that employs an objective lens consisting of small-diameter optical systems as the objective lens of the microscope so that the objective lens can be directly inserted into the living organism to observe the living organism in a minimally invasive manner (for example, see Japanese Unexamined Patent Application, Publication No. 2006-119300).

Conventional microscopes, such as laser-scanning confocal microscopes, are not intended for the observation of the organs of living (in vivo) small laboratory animals, such as rats and mice. However, when the inside of a living organism is to be observed, because the conventional objective lens of the microscope has a large outside diameter, a wide incision needs to be made in the living body for observation. However, because such a wide incision of the living body is highly invasive, long-term observation is impossible.

That is, in order to observe the organs of such small laboratory animals, the skin and muscle tissue need to be incised or the cranium needs to be drilled to expose the internal organs. However, because the size of the objective lens to be disposed close to the observation area is large relative to the small laboratory animal or the observed object, when the internal organs or the like are to be observed, the skin, the muscle tissue, or the like need to be widely incised or provided with a large hole.

On the other hand, Japanese Unexamined Patent Application, Publication No. 2006-119300 discloses an optical system having a small diameter at the tip. However, this is still highly invasive when a deep part of a relatively small organ, such as the brain, of a mouse is to be observed, and, considering the damage to the living body, there is an inconvenience in that observation under normal conditions is difficult. Furthermore, this optical system has problems not only in that it has a small numerical aperture for observation using multiphoton excitation, decreasing the resolution, but also in that it has a poor S/N due to weak detected light.

Moreover, when a deep part of a relatively small organ, such as the brain, of a mouse or a deep part of a living body portion susceptible to damage due to invasion is to be observed with a conventional objective optical system, such as one disclosed in Japanese Unexamined Patent Application, Publication No. 2006-119300, an invasive portion of the objective optical system needs to be designed as thin as possible. However, there is an inconvenience in that the more the diameter of the tip of the objective lens is reduced, the more the field of view (FOV) is narrowed.

In order to microscopically observe living tissue, such as cells and muscles, or various organs, such as the heart and the liver, in particular, the brain tissue, of living mammals, such as small laboratory animals, for a relatively long time in a minimally invasive manner, the diameter of the tip needs to be further reduced. However, further reduction in conventional small-diameter objective lens increases the occurrence of aberrations, such as spherical aberration and field curvature, causing an inconvenience when microscopic observation is performed. This causes a similar inconvenience when observation is to be performed with a wider field of view using the conventional small-diameter objective lens.

BRIEF SUMMARY OF THE INVENTION

The present invention has been made in view of the above-described circumstances, and an object thereof is to provide an objective optical system that enables observation of living tissue, such as cells and muscles, and various organs, such as the heart and the liver, in particular, the brain tissue, of living mammals, such as small laboratory animals, for a relatively long time in a minimally invasive manner and that is used for multiphoton excitation.

Another object of the present invention is to provide an objective optical system capable of performing accurate observation without reducing the object-side numerical aperture as much as possible while reducing the field curvature. Still another object of the present invention is to provide an objective optical system capable of achieving a further reduction in diameter of the tip and/or an increase in the field of view without significantly reducing the object-side numerical aperture, while maintaining the field curvature at a low level.

To achieve the above-described objects, the present invention provides the following solutions.

The present invention provides an objective optical system including, in sequence from an object side, a first group having positive refractive power; a second group having positive refractive power; a third group having negative refractive power; a fourth group having positive refractive power; and a fifth group having positive refractive power. The first group includes a plano-convex lens with a convex surface facing towards an image side, the second group includes a lens whose extreme-object-side lens surface is a convex surface facing towards the object side, the third group includes a lens whose extreme-object-side lens surface is a convex surface facing towards the object side, the fourth group includes a lens disposed on the extreme object side, whose image-side lens surface is a convex surface facing towards the image side, and a lens disposed on the extreme image side, whose object-side lens surface is a convex surface facing towards the object side, and the fifth group includes a combined lens formed by joining a convex lens and a concave lens, a joined surface thereof having negative refractive power. The objective optical system is designed to focus at infinity and has an intermediate image plane between the fourth group and the fifth group.

According to the present invention, in the first group having positive refractive power, by making the extreme object side substantially flat, entry of air bubbles into the space can be prevented. Furthermore, by including the plano-convex lens with the convex surface facing towards the image plane side, the aplanatic condition is nearly satisfied. Thus, the occurrence of spherical aberration and coma can be reduced.

In the second group having positive refractive power, by making the lens surface on the extreme object side, which is a convex surface, face towards the object side, large spherical aberration and coma occur. However, because divergence of a beam can be reduced to prevent an increase in beam height in the second and subsequent groups, the outside diameter of the lenses can be reduced.

In the third group having negative refractive power, by making the lens surface on the extreme image plane side, which is a concave surface, face towards the image plane side, the Petzval sum can be reduced without increasing the beam height in the third group. Thus, field curvature can be corrected.

In the fourth group having positive refractive power, by making the lens surface on the image plane side of the lens disposed on the extreme object side, which is a convex surface, face towards the image plane side, the aplanatic condition is nearly satisfied. Thus, the diverging light from the third group can be converted into substantially converging light without increasing the occurrence of spherical aberration and coma. Furthermore, by making the lens surface on the object side of the lens disposed on the extreme image side, which is a convex surface, face towards the object side, the aplanatic condition is nearly satisfied. Thus, conversion into converging light is possible without increasing the occurrence of spherical aberration and coma.

In the fifth group having positive refractive power, by making the fifth group have positive refractive power as a whole to convert the diverging light into collimated light, and by including a combined lens having the joined surface with negative refractive power, the spherical aberration and chromatic aberration, which cannot be sufficiently corrected by the first to fourth groups, can be corrected.

Furthermore, by providing the intermediate image plane within this objective optical system, the image-side exit pupil can be disposed outside the lenses.

Accordingly, with the thus-configured objective optical system of the present invention, designed to focus at infinity and having an intermediate image plane, it is possible to achieve an objective optical system which has a small outside diameter and a large overall length, can excellently correct various aberrations, has such a high numerical aperture that it can be used for multiphoton excitation, is suited for in vivo observation, is designed to focus at infinity and has the intermediate image plane.

In the above-described invention, it is preferable that the following conditional expression (1) be satisfied:

$$0.15 < F_{12}/(t_{13} \cdot NA) < 0.25 \qquad (1)$$

where $F_{12}$ is the combined focal length of the first and second groups, $t_{13}$ is the optical axis length from the object plane to the surface on the extreme image side of the third group, and NA is the object-side numerical aperture of the objective optical system designed to focus at infinity and having an intermediate image plane.

If conditional expression (1) is smaller than 0.15, the combined focal length of the first and second groups, $F_{12}$, decreases. This increases the refractive power of the first and second groups, which causes large spherical aberration, making correction thereof difficult. Furthermore, an increase in NA on the object side increases the beam height in the first and second groups, making a reduction in diameter impossible. Moreover, an increase in $t_{13}$ increases the length of the small diameter portion of this objective optical system, causing vignetting of off-axis light. This narrows the field of view, which is inconvenient.

In contrast, if conditional expression (1) is larger than 0.25, the combined focal length of the first and second groups, $F_{12}$, increases, which decreases the refractive power. As a result, the diverging light from the object cannot be converged, increasing the beam height in the first and second groups, which is inconvenient. Moreover, a decrease in object-side numerical aperture, NA, leads to an inconvenience, such as a drop of resolution. Moreover, a decrease in $t_{13}$ decreases the length of the small diameter portion of this objective optical system, making observation of a deeper part in a minimally invasive manner difficult, when a deep part of a living body of a small animal, such as a mouse, is observed.

In the above-described invention, it is preferable that the following conditional expressions (2) to (5) be satisfied:

$$12 < F_5/F_{12} < 14 \qquad (2)$$

$$1.7 < \phi_5/\phi_{12} < 2.5 \qquad (3)$$

$$1.75 < n_{12} < 1.90 \qquad (4)$$

$$80 < \nu_5 < 95 \qquad (5)$$

where $F_{12}$ is the combined focal length of the first and second groups, $F_5$ is the focal length of the fifth group, $\phi_{12}$ is the diameter of the smallest lens among the lenses in the first and second groups, $\phi_5$ is the diameter of the largest lens among the lenses in the fifth group, $n_{12}$ is the largest refractive index (d line) among the lenses in the first and second groups, $\nu_5$ is the Abbe number (d line) of the convex lens of the combined lens having the joined surface with negative refractive power in the fifth group.

If conditional expression (2) is smaller than 12, the combined focal length of the first and second groups, $F_{12}$, increases, which decreases the refractive power of the first and second groups. This makes it impossible to converge the diverging light from the object, increasing the beam height in the first and second groups, which is inconvenient.

In contrast, if conditional expression (2) is larger than 14, the focal length of the fifth group, $F_5$, increases. Thus, the diverging light from the fourth group cannot be converted into converging light, which is inconvenient. Furthermore, because a decrease in combined focal length of the first and second groups, $F_{12}$, increases the refractive power of the first and second groups, the first and second groups cause large spherical aberration, which is inconvenient.

If conditional expression (3) is smaller than 1.7, the diameter of the largest lens among the lenses in the fifth group, $\phi_5$, decreases. This makes it difficult to correct various aberrations, such as spherical aberration, caused in the first to fourth groups. Furthermore, because the diameter of the smallest lens among the lenses in the first and second groups, $\phi_{12}$, increases, the diameter cannot be reduced, which is inconvenient.

In contrast, if conditional expression (3) is larger than 2.5, the diameter of the largest lens among the lenses in the fifth group, $\phi_5$, increases, and the diameter of the smallest lens among the lenses in the first and second groups, $\phi_{12}$, decreases. Although this is advantageous to correct aberrations, a too small lens diameter, $\phi_{12}$, results in vignetting of off-axis light, leading to an inconvenience, such as a decrease in object-side numerical aperture, NA, or field of view. Thus, it is preferable that an appropriate value be selected.

If conditional expression (4) is smaller than 1.75, the refractive power of the first and second groups decreases, whereby the diverging light from the object cannot be converged. This increases the beam height and makes a reduction in diameter impossible, which is inconvenient.

In contrast, if conditional expression (4) is larger than 1.90, the radii of curvatures of the first and second groups increase. This results in over-correction of spherical aberration, which is inconvenient.

If conditional expression (5) is smaller than 80, the difference in Abbe number at the joined surface decreases because, normally, a flint glass member with a high refractive index and high dispersion is used for the concave lens of the combined lens. This makes correction of chromatic aberration caused in the first to fourth groups difficult.

In contrast, if conditional expression (5) is larger than 95, the chromatic aberration is over-corrected, which is inconvenient.

In the above-described invention, it is preferable that a lens surface on the extreme object side in the first group be substantially flat, the fifth group include a lens whose surface closest to the intermediate image plane is a concave surface facing towards the intermediate image plane, and an image-side exit pupil be located at the image side of the lens surface positioned on the extreme image side in the objective optical system.

According to this configuration, in the first group having positive refractive power, by making the extreme object side substantially flat, air bubbles can be prevented from entering between the specimen and the objective optical system during immersion observation. Furthermore, by including the convex lens with the convex surface facing towards the image side, the aplanatic condition is nearly satisfied. Thus, divergence of the diverging light from the specimen can be reduced while reducing the occurrence of spherical aberration and coma.

In the second group having positive refractive power, by making the lens surface on the extreme object side, which is a convex surface, face towards the object side, large spherical aberration and coma occur. However, divergence of the beam can be reduced to prevent the beam height from increasing in the second and subsequent groups. Thus, the outside diameter of the lenses can be reduced.

In the third group having negative refractive power, by making the lens surface on the extreme image side, which is a concave surface, face towards the image side, the Petzval sum can be reduced without increasing the beam height in the third group. Thus, field curvature and spherical aberration can be corrected.

In the fourth group having positive refractive power, by making the lens surface on the image side of the lens disposed on the extreme object side, which is a convex surface, face towards the image side, the aplanatic condition is nearly satisfied. Thus, the diverging light from the third group can be converted into substantially converging light without increasing the occurrence of spherical aberration and coma. Furthermore, by making the lens surface on the object side of the lens disposed on the extreme image side, which is a convex surface, face towards the object side, the aplanatic condition is nearly satisfied. Thus, conversion into converging light is possible without increasing the occurrence of spherical aberration and coma.

In the fifth group, by disposing the concave surface near the intermediate image plane, the Petzval sum can be reduced without relatively increasing divergence of light from the intermediate image-forming position. At this time, when the lens surface closest to the intermediate image-forming position of the fourth group, disposed at the object side of the intermediate image plane, is made to have a concave surface to reduce the Petzval sum, because the diverging light from the intermediate image plane is further diverged at the concave surface, the diameter of the lens at the tip increases. If divergence is restricted with a stronger positive refractive power to restrict spreading of the diverging light, spherical aberration occurs, which is inconvenient.

Furthermore, by disposing the concave surface at the image side of the intermediate image plane, the Petzval sum can be reduced to prevent the occurrence of field curvature, and the light-focusing angle of the main beam can be reduced. This enables the image-side exit pupil to be located at the image side of the lens surface disposed on the extreme image side of the objective optical system, making it optically easy to dispose a relay optical system at the image side of this objective optical system.

In the above-described configuration, the intermediate image plane is disposed between the fourth group and the fifth group.

By configuring the system in this manner, although the outside diameter of the lens forming the fifth group is increased, the outside diameter from the first group to the intermediate image plane is kept small. Thus, an objective optical system having a smaller outside diameter can be provided.

In the fifth group having positive refractive power, by making the fifth group have positive refractive power as a whole to convert the diverging light into collimated light, and by including a combined lens having the joined surface with negative refractive power, spherical aberration, chromatic aberration, etc., which cannot be sufficiently corrected by the first to fourth groups, can be corrected.

In the above-described configuration, it is preferable that the following conditional expression (6) be satisfied:

$$0.28 < (t_5 \cdot R_5)/(Dep \cdot FOV) < 0.55 \qquad (6)$$

where $t_5$ is the distance from the intermediate image plane to the surface closest to the intermediate image plane in the fifth group, and $R_5$ is the radius of curvature of the surface closest to the intermediate image plane in the fifth group. Furthermore, Dep is the depth of focus on one side at the intermediate image plane, defined by the following expression:

$$Dep = \lambda/(NA/\beta)^2$$

where $\lambda$ is the wavelength of the d line (587.6 nm), and $\beta$ is the magnification from the object plane to the intermediate image plane. Furthermore, FOV is the field of view on the object side.

An increase in the field of view causes field curvature. To correct such field curvature, conditional expression (6) defines the proper relationship of the field of view, FOV, on the object side of the objective optical system of the present invention, the radius of curvature, $R_5$, of the lens surface closest to the intermediate image plane in the fifth group, with the concave surface facing towards the intermediate image plane, the distance between the lens surface closest to the intermediate image plane in the fifth group and the intermediate image plane, $t_5$, and the depth of focus at the intermediate image plane, Dep.

If conditional expression (6) is smaller than 0.28, $t_5$ decreases. If $t_5$ is small, the radius of curvature, $R_5$, has to be decreased to bend the beam at a low beam height. A decrease in $R_5$ results in over-correction of field curvature, which is inconvenient. An increase in the field of view, FOV, makes correction of field curvature difficult, which is also inconvenient.

In contrast, if conditional expression (6) is larger than 0.55, $t_5$ increases. This conversely increases the radius of curvature, $R_5$, making correction of field curvature impossible, which is inconvenient.

Furthermore, it is preferable that expression (6) fall within the following range to correct aberrations.

$$0.4 < (t_5 \cdot R_5)/(Dep \cdot FOV) < 0.55$$

Accordingly, with the thus-configured present invention, it is possible to provide an objective optical system that has a small outside diameter and a wide field of view, can excellently correct various aberrations, has such a high numerical aperture so that it can be used for two-photon excitation, and is suited for in vivo observation.

In the above-described configuration, it is preferable that the following conditional expressions (7) to (11) be satisfied:

$$0.37 < F_{12}/(t_{13} \cdot NA) < 0.45 \quad (7)$$

$$2.0 < \phi_5/\phi_{12} < 2.5 \quad (8)$$

$$1.75 < n_{12} < 1.90 \quad (9)$$

$$0.27 < \Delta n_5 < 0.45 \quad (10)$$

$$30 < \Delta v_5 < 55 \quad (11)$$

where
- $F_{12}$: combined focal length of the first and second groups;
- $t_{13}$: optical axis length from the object plane to the image side surface of the third group;
- NA: object-side numerical aperture;
- $\phi_5$: diameter of the largest lens among the lenses in the fifth group;
- $\phi_{12}$: diameter of the smallest lens among the lenses in the first and second groups;
- $n_{12}$: largest refractive index (d line) among the lenses in the first and second groups;
- $\Delta n_5$: difference in refractive index (d line) of the combined lens having the joined surface with negative refractive power in the fifth group; and
- $\Delta v_5$: difference in Abbe number (d line) of the combined lens having the joined surface with negative refractive power in the fifth group.

Conditional expression (7) defines the relationship of the combined focal length of the first and second groups, $F_{12}$, the optical axis length from the object plane to the surface on the extreme image side of the third group, $t_{13}$, and the object-side numerical aperture, NA, which is preferable to correct aberrations due to the reduced diameter of the tip.

If conditional expression (7) is smaller than 0.37, the combined focal length of the first and second groups, $F_{12}$, decreases, which increases the refractive power of the first and second groups. This causes severe spherical aberration, making correction thereof difficult. Furthermore, an increase in object-side numerical aperture, NA, causes severe spherical aberration, making correction thereof difficult.

In contrast, if conditional expression (7) is larger than 0.45, the combined focal length of the first and second groups, $F_{12}$, increases, which decreases the refractive power. This results in an inconvenience, such as over-correction of spherical aberration. Otherwise, a decrease in object-side numerical aperture, NA, causes over-correction of aberration, such as spherical aberration, which is inconvenient.

Conditional expression (8) relates to a condition for realizing an optical system that is maximally thin and long, while maintaining aberrations at a favorable level, when both the FOV with respect to the object on the specimen surface and the numerical aperture are increased. That is, when both the FOV with respect to the object on the specimen surface and the numerical aperture are increased, because the diverging light from the specimen surface becomes more readily spreadable, if the light is left as it is, the diameter of the optical system on the image side increases. Thus, a high power optical system that converts the beam, in the opposite way, into substantially converging light is employed. At this time, immediately after the lens closest to the object forms a highly diverging beam, the lens second closest to the object drastically narrows the beam in a converging direction. This drastic change in divergence angle brings about a problem in that the small diameter portion at the tip causes relatively large aberrations (mainly spherical aberration). Therefore, in the present invention, the aberration caused at the tip is corrected by increasing the beam diameter at the fifth group. For that purpose, conditional expression (3) defines the relationship between the outside diameter of the smallest lens in the first and second groups and the outside diameter of the largest lens in the fifth group. In the present invention, by defining the ratio of the diameter of the smallest lens among the lenses in the first and second groups to the diameter of the largest lens among the lenses in the fifth group, 1:2.0 to 2.5, to satisfy conditional expression (8), the diverging light from the specimen surface can be converged without being spread. Thus, various aberrations can be sufficiently corrected, while maintaining a long, thin shape.

If conditional expression (8) is smaller than 2.0, the diameter of the largest lens among the lenses in the fifth group, $\phi_5$, decreases. This makes it difficult to correct, in the fifth group, various aberrations, such as spherical aberration, caused in the first to fourth groups.

In contrast, if conditional expression (8) is larger than 2.5, the diameter of the largest lens among the lenses in the fifth group, $\phi_5$, increases. This decreases the diameter of the smallest lens among the lenses in the first and second groups, $\phi_{12}$, leading to over-correction, in the fifth group, of the various aberrations, such as spherical aberration, caused in the first to fourth groups.

Regarding conditional expression (9), although the refractive power of the first and second groups at the tip portion has to be increased to reduce the diameter of the tip, it is preferable that the largest refractive index among the lenses in the first and second groups be set to an appropriate value to correct aberrations.

If conditional expression (9) is smaller than 1.75, the radii of curvatures of the first and second groups decrease. This results in under-correction of spherical aberration and causes field curvature, which are inconvenient.

In contrast, if conditional expression (9) is larger than 1.90, the radii of curvatures of the first and second groups increase. This results in over-correction of spherical aberration and field curvature, which is inconvenient.

Conditional expression (10) defines the difference in refractive index, $\Delta n_5$, of the combined lens having the joined surface with negative refractive power in the fifth group (d line) to correct aberrations, such as spherical aberration, caused in the first to fourth groups.

If conditional expression (10) is smaller than 0.27, the difference in refractive index at the joined surface having negative refractive power decreases, making correction of aberrations, such as spherical aberration, caused in the first to fourth groups difficult.

In contrast, if conditional expression (10) is larger than 0.45, the difference in refractive index at the joined surface having negative refractive power increases, resulting in an inconvenience such as over-correction of aberrations or an increase in beam height.

Conditional expression (11) defines the difference in Abbe number, $\Delta v_5$, of the combined lens having the joined surface with negative refractive power in the fifth group (d line) to correct chromatic aberration caused in the first to fourth groups.

If conditional expression (11) is smaller than 30, chromatic aberration is under-corrected.

In contrast, if conditional expression (11) is larger than 55, the chromatic aberration is over-corrected, which is inconvenient.

Furthermore, the above-described configuration may include an outer cylinder having a substantially uniform diameter that accommodates the first to third groups.

Furthermore, in the above-described configuration, the average inside diameter of the outer cylinder may be 1 mm or less.

Furthermore, in the above-described configuration, the dimensional ratio of the outside diameter to length of the outer cylinder may be 1:10 or more.

Furthermore, in the above-described configuration, the outer cylinder may have an outside diameter of about 1.8 mm or less and a length of about 20 mm or more.

Furthermore, in the above-described configuration, it is preferable that the field of view on the object side be 0.25 or more and the object-side numerical aperture be 0.35 or more.

The present invention has advantages in that it enables observation of living tissue, such as cells and muscles, and various organs, such as the heart and the liver, in particular, the brain tissue, of living mammals, such as small laboratory animals, for a relatively long time in a minimally invasive manner, and it can be used for multiphoton excitation.

The present invention also has advantages in that it can increase the field of view, while maintaining the small diameter, it can reduce field curvature, and it enables accurate observation with a high numerical aperture. Furthermore, the present invention also has advantages in that it realizes a further reduction in diameter of the tip and/or a further increase in the field of view, while maintaining the field curvature at a low level, and it enables accurate observation with a high numerical aperture.

DETAILED DESCRIPTION OF THE INVENTION

First Embodiment

Figure 1:
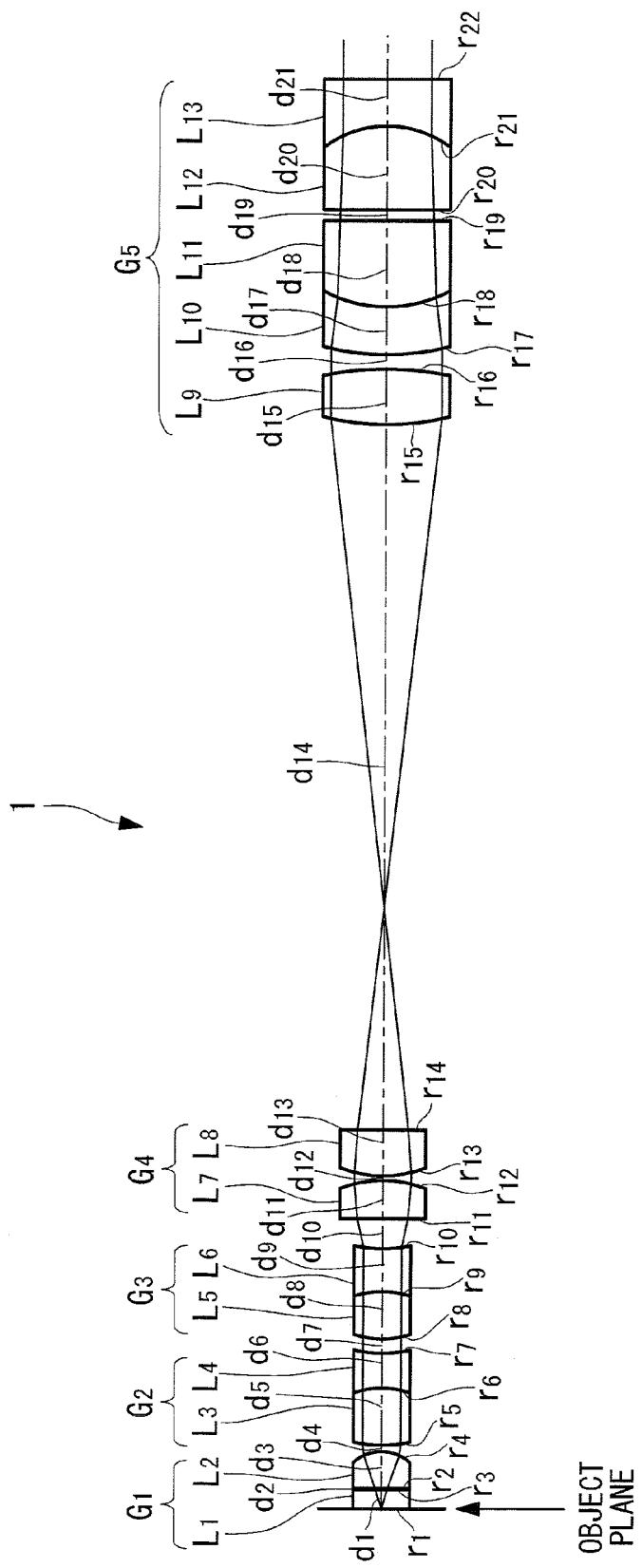
FIG. 1 is a diagram showing the structure of an objective optical system according to a first embodiment of the present invention.

FIG. 1 shows the lens configuration according to a first embodiment of the present invention, and the first embodiment will be described below.

An immersion small-diameter objective optical system 1 according to this embodiment, designed to focus at infinity and having an intermediate image plane, includes a first group $G_1$ having positive refractive power, including a lens disposed on the extreme object side, whose object-side lens surface is substantially flat, and a plano-convex lens with the convex surface facing towards the image plane side; a second group $G_2$ having positive refractive power, whose extreme-object-side lens surface is a convex surface facing towards the object side; a third group $G_3$ having negative refractive power, whose lens surface on the extreme image plane side is a concave surface facing towards the image plane side; a fourth group $G_4$ having positive refractive power, whose lens surface, on the image plane side, of the lens disposed on the extreme object side is a convex surface facing towards the image plane side and whose object-side lens surface of the lens disposed on the extreme image side is a convex surface facing towards the object side; a fifth group $G_5$ having positive refractive power including combined lenses, each consisting of a convex lens and a concave lens and having negative refractive power at the joined surface; and the intermediate image plane disposed between the fourth group $G_4$ and the fifth group $G_5$.

More specifically, the first lens group $G_1$ having positive refractive power includes a parallel plate $L_1$ and a plano-convex lens $L_2$ with the convex surface facing towards the image plane side and having a d-line refractive index of 1.883.

The second lens group $G_2$ having positive refractive power includes a combined lens formed by joining a biconvex lens $L_3$ whose object-side surface is a convex surface facing towards the object side and a biconcave lens $L_4$.

The third lens group $G_3$ having negative refractive power includes a combined lens formed by joining a biconvex lens $L_5$ and a biconcave lens $L_6$ whose image-side surface is a concave surface facing towards the image plane side.

The fourth lens group $G_4$ having positive refractive power as a whole includes a biconvex lens $L_7$ disposed on the extreme object side, whose image-side lens surface is a convex surface facing towards the image side and a plano-convex lens $L_8$ disposed on the extreme image side, whose object-side lens surface is a convex surface facing towards the object side.

The fifth lens group $G_5$ having positive refractive power as a whole includes a biconvex lens $L_9$, a combined lens formed by joining a meniscus lens $L_{10}$ with the concave surface facing towards the image side, having negative refractive power, and a plano-convex lens $L_{11}$ with the convex surface facing towards the object side, having positive refractive power, the combined lens having negative refractive power at the joined surface, and a combined lens formed by joining a plano-convex lens $L_{12}$ with the convex surface facing towards the image side, having positive refractive power, and a meniscus lens $L_{13}$ with the concave surface facing towards the object side, having negative refractive power, the combined lens having negative refractive power at the joined surface. The plano-convex lenses $L_{11}$ and $L_{12}$ have an Abbe number of 94.9.

The image-side exit pupil is disposed at the image side, 1.3 mm away from the meniscus lens $L_{13}$.

In this embodiment, the lenses $L_1$ to $L_{13}$ are configured to satisfy the following conditional expressions (1) to (5).

$$0.15 < F_{12}/(t_{13} \cdot NA) < 0.25 \quad (1)$$

$$12 < F_5/F_{12} < 14 \quad (2)$$

$$1.7 < \phi_5/\phi_{12} < 2.5 \quad (3)$$

$$1.75 < n_{12} < 1.90 \quad (4)$$

$$80 < \nu_5 < 95 \quad (5)$$

where $F_{12}$ is the combined focal length of the first group $G_1$ and the second group $G_2$, $t_{13}$ is the optical axis length from the object plane to the surface on the extreme image side of the third group $G_3$, NA is the object-side numerical aperture of the objective optical system 1 designed to focus at infinity and having an intermediate image plane, $F_5$ is the focal length of the fifth group $G_5$, $\phi_{12}$ is the diameter of the smallest lens among the lenses $L_1$ to $L_4$ in the first group $G_1$ and the second group $G_2$, $\phi_5$ is the diameter of the largest lens among the lenses $L_9$ to $L_{13}$ in the fifth group $G_5$, $n_{12}$ is the largest refractive index (d line) among the lenses $L_1$ to $L_4$ of the first group $G_1$ and the second group $G_2$, and $\nu_5$ is the Abbe number (d line) of the plano-convex lens $L_{11}$ of the combined lens of the fifth group $G_5$ having negative refractive power at the joined surface.

Figure 3:
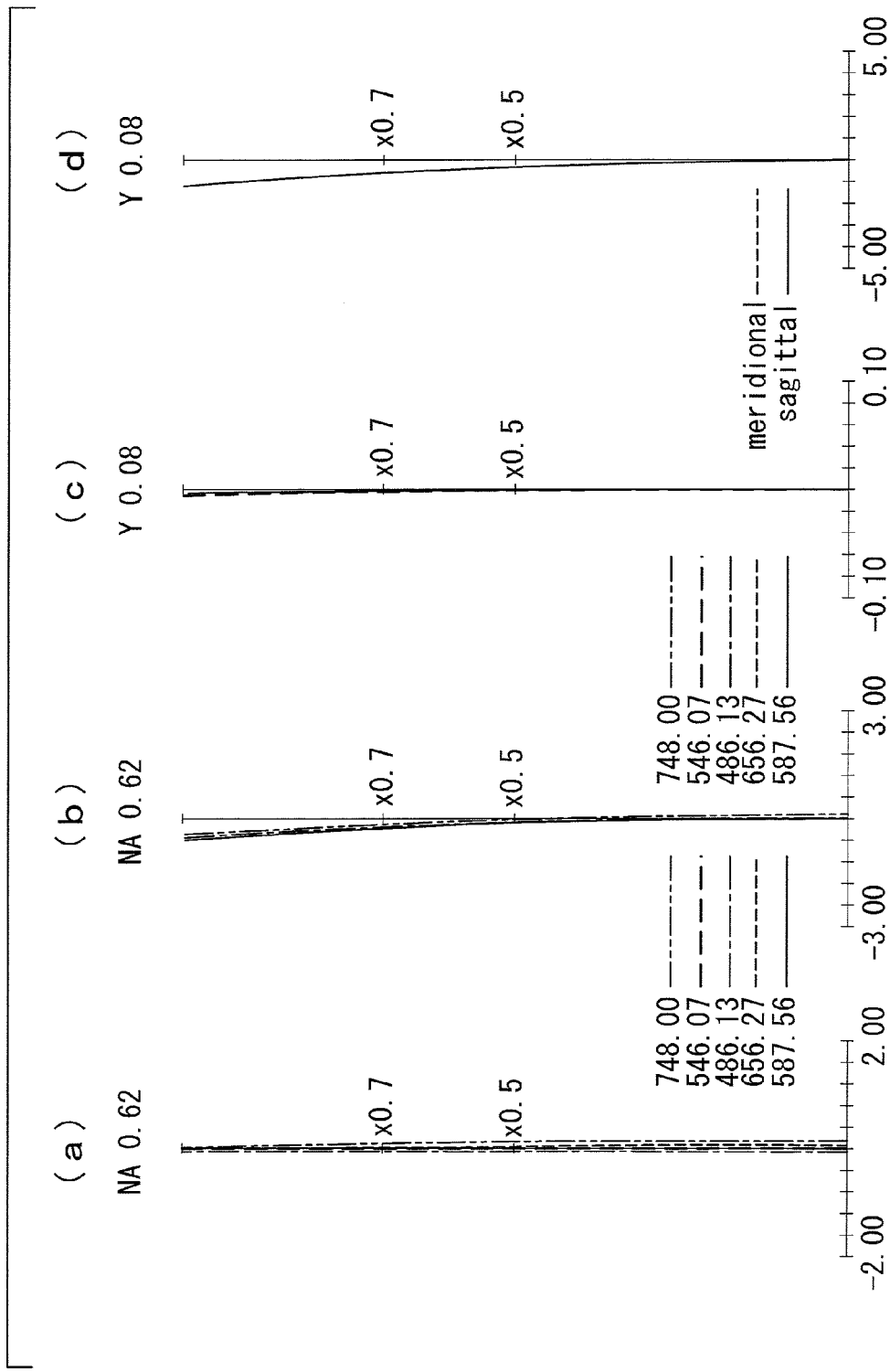
FIG. 3 contains aberration diagrams of the objective optical system according to the first embodiment of the present invention, showing (a) spherical aberration, (b) the offence against the sine condition, (c) astigmatism, and (d) distortion.

Table 1 shows the lens data of the objective optical system 1 according to this embodiment, and FIG. 3 shows aberration diagrams of this embodiment.

TABLE 1

| SURFACE NO. | r | d | nd | νd |
|---|---|---|---|---|
| OBJECT PLANE | ∞ | 0.03 (WORKING DISTANCE) | 1.333 (WATER) | 55 |
| 1 | ∞ | 0.24 | 1.883 | 40.8 |
| 2 | ∞ | 0.03 | 1.333 (WATER) | 55 |
| 3 | ∞ | 0.53 | 1.883 | 40.8 |
| 4 | −0.54 | 0.08 | | |
| 5 | 1.5 | 0.8 | 1.773 | 49.6 |
| 6 | −1.5 | 0.5 | 1.613 | 44.3 |
| 7 | 1.5 | 0.2 | | |
| 8 | 1.18 | 0.67 | 1.487 | 70.2 |

TABLE 1-continued

| SURFACE NO. | r | d | nd | νd |
|---|---|---|---|---|
| 9 | −1.5 | 0.62 | 1.883 | 40.8 |
| 10 | 1.5 | 0.4 | | |
| 11 | 5.2 | 0.58 | 1.678 | 55.3 |
| 12 | −1.72 | 0.08 | | |
| 13 | 2.1 | 0.65 | 1.487 | 70.2 |
| 14 | ∞ | 10.1 | | |
| 15 | 4.38 | 0.8 | 1.439 | 94.9 |
| 16 | −4.38 | 0.2 | | |
| 17 | 4.38 | 0.67 | 1.773 | 49.6 |
| 18 | 1.82 | 1.2 | 1.439 | 94.9 |
| 19 | ∞ | 0.15 | | |
| 20 | ∞ | 1.2 | 1.439 | 94.9 |
| 21 | −1.43 | 0.68 | 1.613 | 44.3 |
| 22 | −12.51 | | | |

The symbols in the table are as follows:
r: radius of curvature, d: distance between surfaces, nd: refractive index (d line), and νd: Abbe number (d line).

In this embodiment, the values in conditional expressions (1) to (5) are as follows:

$F_{12} = 0.418$ $F_5 = 5.50$ $t_{13} = 3.70$

NA = 0.62

$\phi_{12} = 0.80$ $\phi_5 = 1.80$ $n_{12} = 1.883$ $\nu_5 = 94.9$ $$F_{12}/(t_{13} \cdot NA) = 0.18 \quad (1)$$

$$F_5/F_{12} = 13.2 \quad (2)$$

$$\phi_5/\phi_{12} = 2.25 \quad (3)$$

$$n_{12} = 1.883 \quad (4)$$

$$\nu_5 = 94.9 \quad (5)$$

In the objective optical system 1 according to this embodiment, the lenses $L_1$ to $L_6$ have a diameter of 0.8 mm, the lenses $L_7$ and $L_8$ have a diameter of 1.2 mm, and the lenses $L_9$ to $L_{13}$ have a diameter of 1.8 mm. The tip portion, i.e., from the lenses $L_1$ to $L_6$, consists only of the lenses having a very small diameter.

Therefore, this is suitable for performing in vivo observation of a deep part of the body of a small laboratory animal, such as a mouse, in a minimally invasive manner for a relatively long time. Furthermore, in this embodiment, aberration is corrected up to the near-infrared region. Thus, it is possible to observe not only the surface of a specimen, but also the inside of the living body using near-infrared light with relatively little influence by diffusion. Furthermore, because the object-side numerical aperture is relatively large, it can also be used for multiphoton excitation.

Second Embodiment

Figure 2:
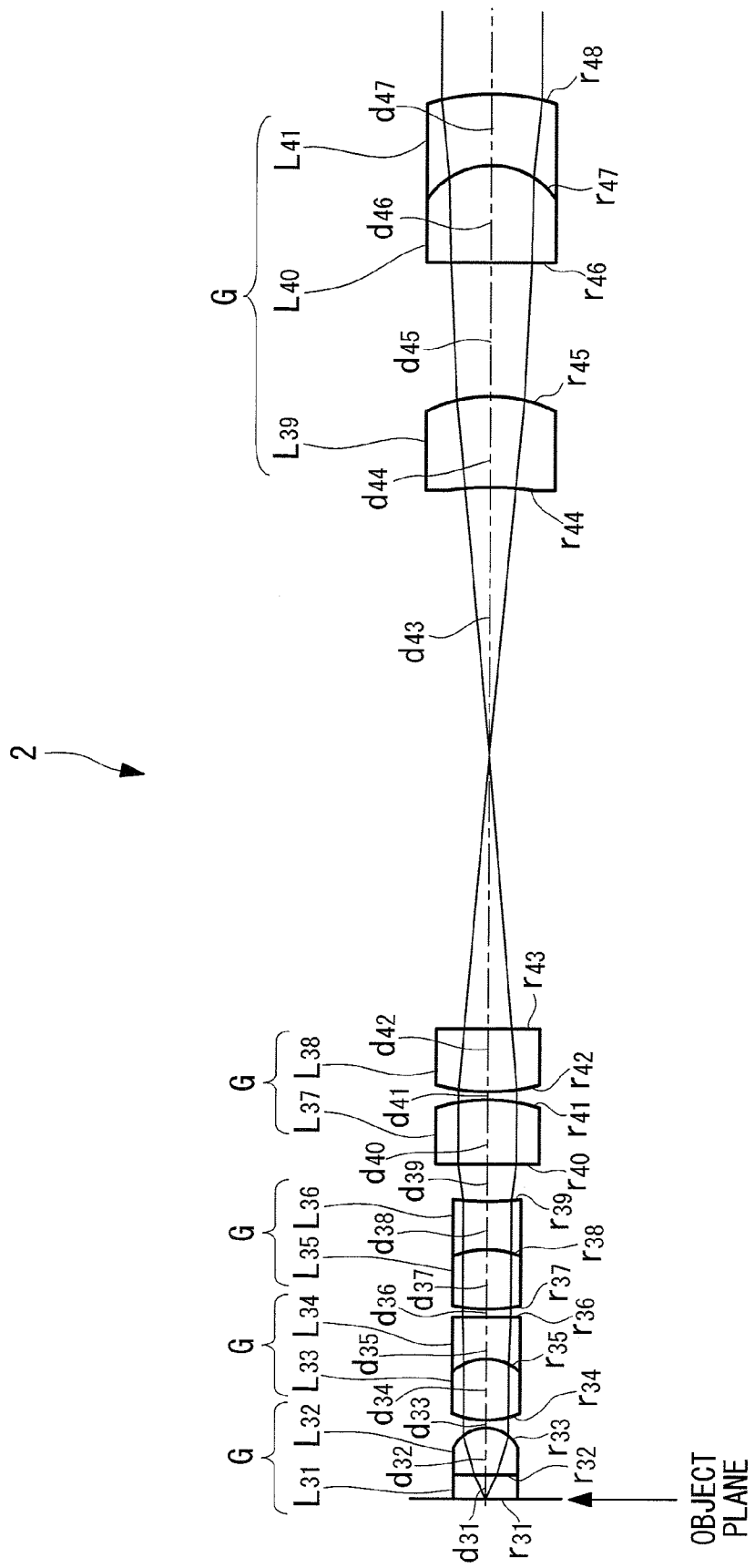
FIG. 2 is a diagram showing the structure of an objective optical system according to a second embodiment of the present invention.

FIG. 2 shows the lens configuration according to a second embodiment of the present invention, and the second embodiment will be described below.

The structures that are common to those of the first embodiment will be denoted by the same reference numerals.

An objective optical system 2 according to this embodiment, designed to focus at infinity and having an intermediate image plane, includes a first group $G_1$ having positive refractive power, including a lens disposed on the extreme object side, whose object-side lens surface is substantially flat, and a plano-convex lens with the convex surface facing towards the image plane side; a second group $G_2$ having positive refractive power, whose extreme-object-side lens surface is a convex surface facing towards the object side; a third group $G_3$ having negative refractive power, whose lens surface on the extreme image plane side is a concave surface facing towards the image plane side; a fourth group $G_4$ having positive refractive power, whose lens surface, on the image plane side, of the lens disposed on the extreme object side is a convex surface facing towards the image plane side and whose object-side lens surface of the lens disposed on the extreme image side is a convex surface facing towards the object side; a fifth group $G_5$ having positive refractive power including a combined lens consisting of a convex lens and a concave lens and having negative refractive power at the joined surface; and the intermediate image plane disposed between the fourth group $G_4$ and the fifth group $G_5$.

More specifically, the first group $G_1$ having positive refractive power includes a parallel plate $L_{31}$ and a plano-convex lens $L_{32}$ with the convex surface facing towards the image plane side and having a d-line refractive index of 1.883.

The second group $G_2$ having positive refractive power includes a combined lens formed by joining a biconvex lens $L_{33}$ whose object-side surface is a convex surface facing towards the object side and a plano-concave lens $L_{34}$.

The third group $G_3$ having negative refractive power includes a combined lens formed by joining a biconvex lens $L_{35}$ and a biconcave lens $L_{36}$ whose image-side surface is a concave surface facing towards the image plane side.

The fourth group $G_4$ having positive refractive power as a whole includes a plano-convex lens $L_{37}$ disposed on the extreme object side, whose image-side lens surface is a convex surface facing towards the image side and a plano-convex lens $L_{38}$ disposed on the extreme image side, whose object-side lens surface is a convex surface facing towards the object side.

The fifth lens group $G_5$ having positive refractive power as a whole includes a meniscus lens $L_{39}$ with the convex surface facing towards the image side, having positive refractive power, and a combined lens formed by joining a plano-convex lens $L_{40}$ with the convex surface facing towards the image side, having positive refractive power, and a meniscus lens $L_{41}$ with the convex surface facing towards the image side, having negative refractive power, the combined lens having negative refractive power at the joined surface. The plano-convex lens $L_{40}$ has an Abbe number of 94.9.

The image-side exit pupil is disposed at the image side, 4.8 mm away from the meniscus lens $L_{41}$.

In this embodiment, the lenses $L_{31}$ to $L_{41}$ are configured to satisfy the following conditional expressions (1) to (5).

$$0.15 < F_{12}/(t_{13} \cdot NA) < 0.25 \quad (1)$$

$$12 < F_5/F_{12} < 14 \quad (2)$$

$$1.7 < \phi_5/\phi_{12} < 2.5 \quad (3)$$

$$1.75 < n_{12} < 1.90 \quad (4)$$

$$80 < v_5 < 95 \quad (5)$$

where $F_{12}$ is the combined focal length of the first group $G_1$ to the second group $G_2$, $t_{13}$ is the optical axis length from the object plane to the surface on the extreme image side of the third group $G_3$, NA is the object-side numerical aperture of the objective optical system 2 designed to focus at infinity and having an intermediate image plane, $F_5$ is the focal length of the fifth group $G_5$, $\phi_{12}$ is the diameter of the smallest lens among the lenses $L_{31}$ to $L_34$ in the first group $G_1$ and the second group $G_2$, $\phi_5$ is the diameter of the largest lens among the lenses $L_{39}$ to $L_{41}$ in the fifth group $G_5$, $n_{12}$ is the largest refractive index (d line) among the lenses $L_{31}$ to $L_{34}$ of the first group $G_1$ and the second group $G_2$, and $v_5$ is the Abbe number (d line) of the convex lens $L_{40}$ of the combined lens of the fifth group $G_5$ having negative refractive power at the joined surface.

Figure 4:
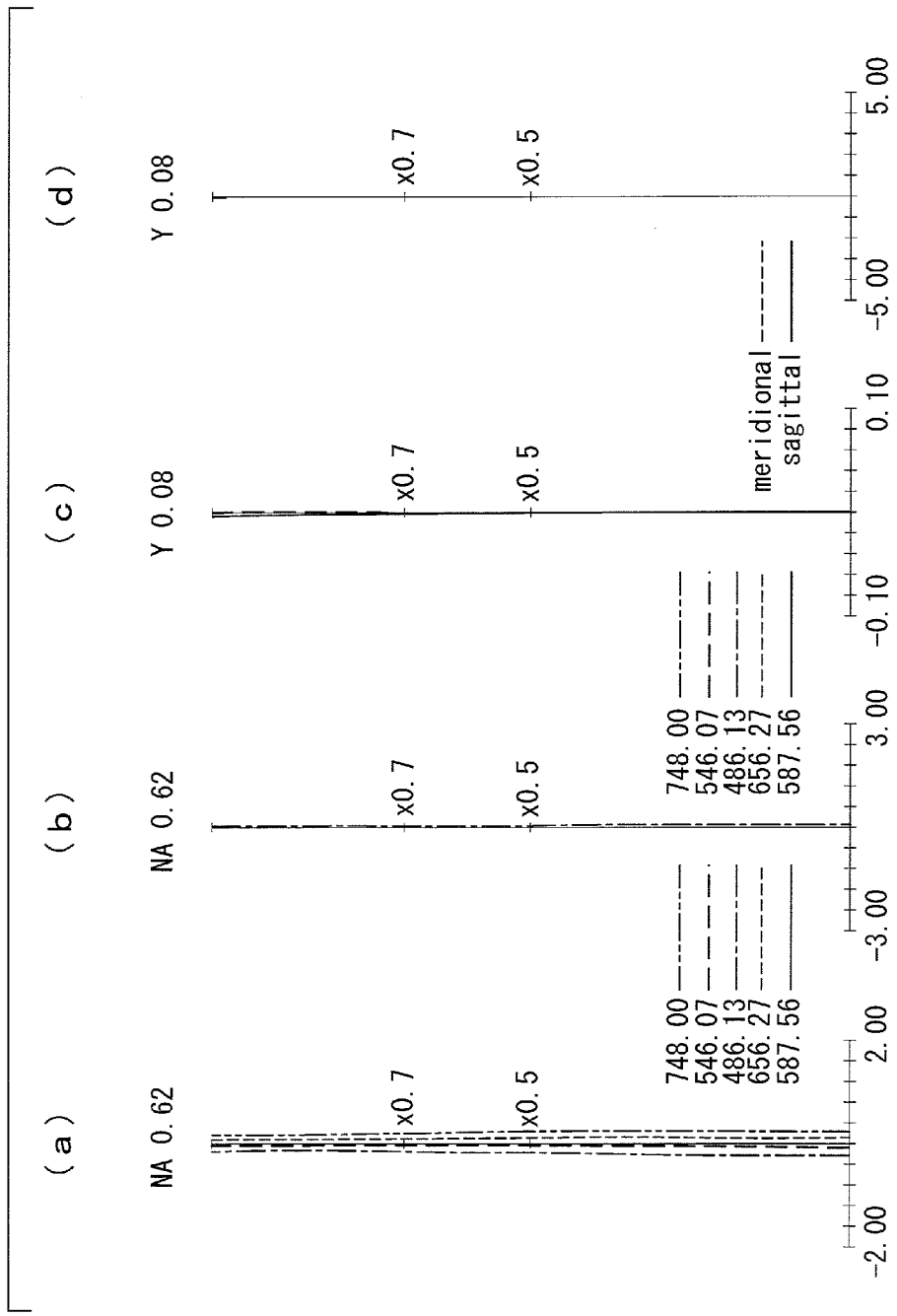
FIG. 4 contains aberration diagrams of the objective optical system according to the second embodiment of the present invention, showing (a) spherical aberration, (b) the offence against the sine condition, (c) astigmatism, and (d) distortion.

Table 2 shows the lens data of the objective optical system 2 according to this embodiment, and FIG. 4 shows aberration diagrams of this embodiment.

TABLE 2

| SURFACE NO. | r | d | nd | vd |
|---|---|---|---|---|
| OBJECT PLANE | ∞ | 0.03 (WORKING DISTANCE) | 1.333 (WATER) | 55 |
| 31 | ∞ | 0.3 | 1.773 | 49.6 |
| 32 | ∞ | 0.57 | 1.883 | 40.8 |
| 33 | −0.49 | 0.1 | | |
| 34 | 1.61 | 0.8 | 1.439 | 94.9 |
| 35 | −0.56 | 0.5 | 1.613 | 44.3 |
| 36 | ∞ | 0.1 | | |
| 37 | 1.5 | 0.75 | 1.439 | 94.9 |
| 38 | −1.5 | 0.6 | 1.613 | 44.3 |
| 39 | 1.51 | 0.5 | | |
| 40 | ∞ | 0.8 | 1.678 | 55.3 |
| 41 | −2.33 | 0.1 | | |
| 42 | 2.05 | 0.8 | 1.487 | 70.2 |
| 43 | ∞ | 6.9 | | |
| 44 | −3.87 | 1.15 | 1.439 | 94.9 |
| 45 | −2.1 | 1.7 | | |
| 46 | ∞ | 1.25 | 1.439 | 94.9 |
| 47 | −0.98 | 0.9 | 1.613 | 44.3 |
| 48 | −2.59 | | | |

Although the objective optical system 2 according to this embodiment is basically the same as that according to the first embodiment, this is an example in which distortion is corrected and image distortion is reduced compared to the first embodiment.

Furthermore, in this embodiment too, the lenses $L_{31}$ to $L_{36}$ have a diameter of 0.8 mm and the lenses $L_{37}$ and $L_{38}$ have a diameter of 1.2 mm, and the tip portion consists only of the lenses having a very small diameter.

Therefore, this is suitable for performing in vivo observation of a deep part of the body of a small laboratory animal, such as a mouse, in a minimally invasive manner for a relatively long time. Furthermore, aberration is corrected up to the near-infrared region. Thus, it is possible to observe not only the surface of a specimen, but also the inside of the living body using near-infrared light with relatively little influence by diffusion. Furthermore, because the object-side numerical aperture is relatively large, it can also be used for multiphoton excitation.

In this embodiment, the values in conditional expressions (1) to (5) are as follows:

$F_{12}=0.470$ $F_5=6.07$ $t_{13}=3.72$ $NA=0.61$ $\phi_{12}=0.80$ $\phi_5=1.60$ $n_{12}=1.883$ $v_5=94.9$ $F_{12}/(t_{13} \cdot NA)=0.20$ (1)

$F_5/F_{12}=12.9$ (2)

$\phi_5/\phi_{12}=2.00$ (3)

$n_{12}=1.883$ (4)

$v_5=94.9$ (5)

Figure 5:
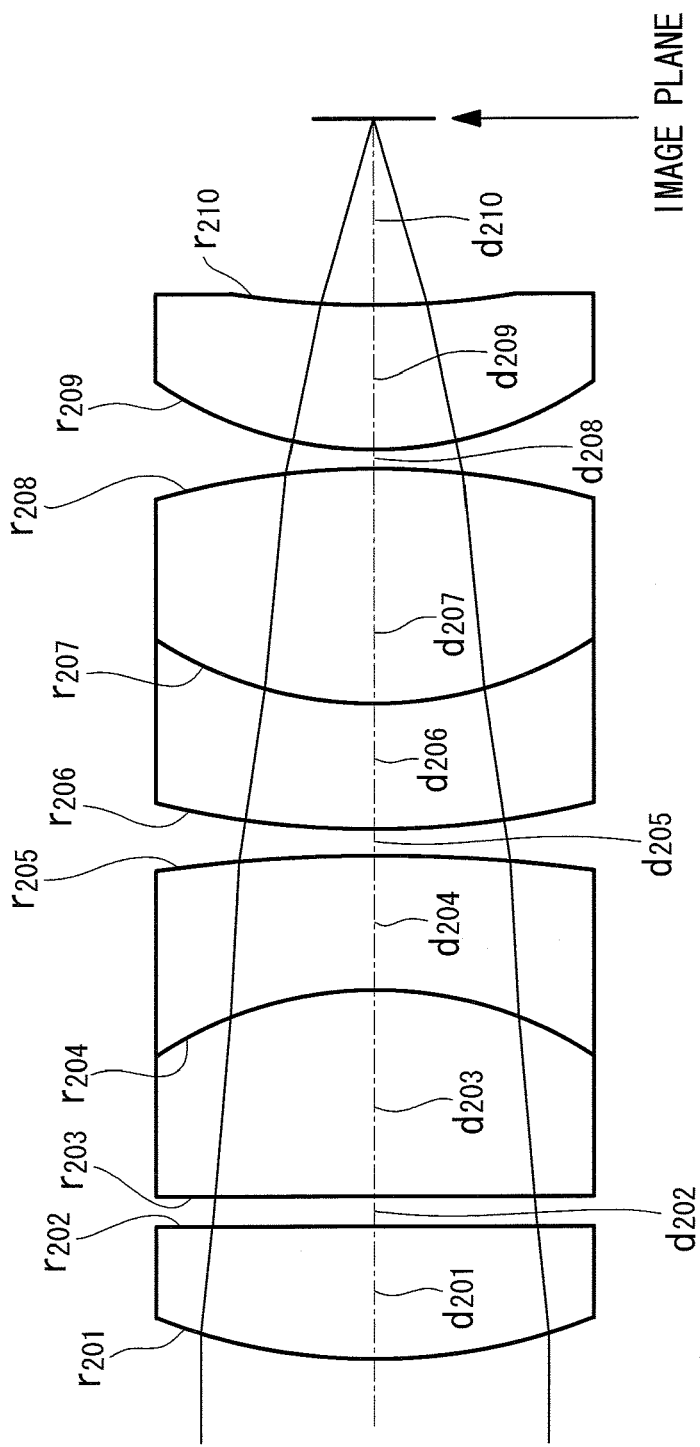
FIG. 5 is a diagram showing the structure of an exemplary image-forming lens.

Note that, in both the first and second embodiments, because the light exiting towards the image side is collimated light, the objective optical system itself forms no image. Therefore, it is used in combination with an image-forming lens having the lens data shown in Table 3 below and having the lens configuration as shown in FIG. 5.

TABLE 3

| SURFACE NO. | r | d | nd | vd |
|---|---|---|---|---|
| 201 | 2.59 | 0.54 | 1.487 | 70.2 |
| 202 | ∞ | 0.12 | | |
| 203 | ∞ | 0.85 | 1.439 | 94.9 |
| 204 | −1.57 | 0.54 | 1.613 | 44.3 |
| 205 | −5.63 | 0.1 | | |
| 206 | 3.9 | 0.5 | 1.613 | 44.3 |
| 207 | 1.65 | 0.95 | 1.439 | 94.9 |
| 208 | −3.6 | 0.1 | | |
| 209 | 1.67 | 0.59 | 1.487 | 70.2 |
| 210 | 5.1 | 0.74 | | |
| IMAGE PLANE | | | | |

Third Embodiment

An objective optical system 3 according to a third embodiment of the present invention will be described with reference to the drawings.

Figure 6:
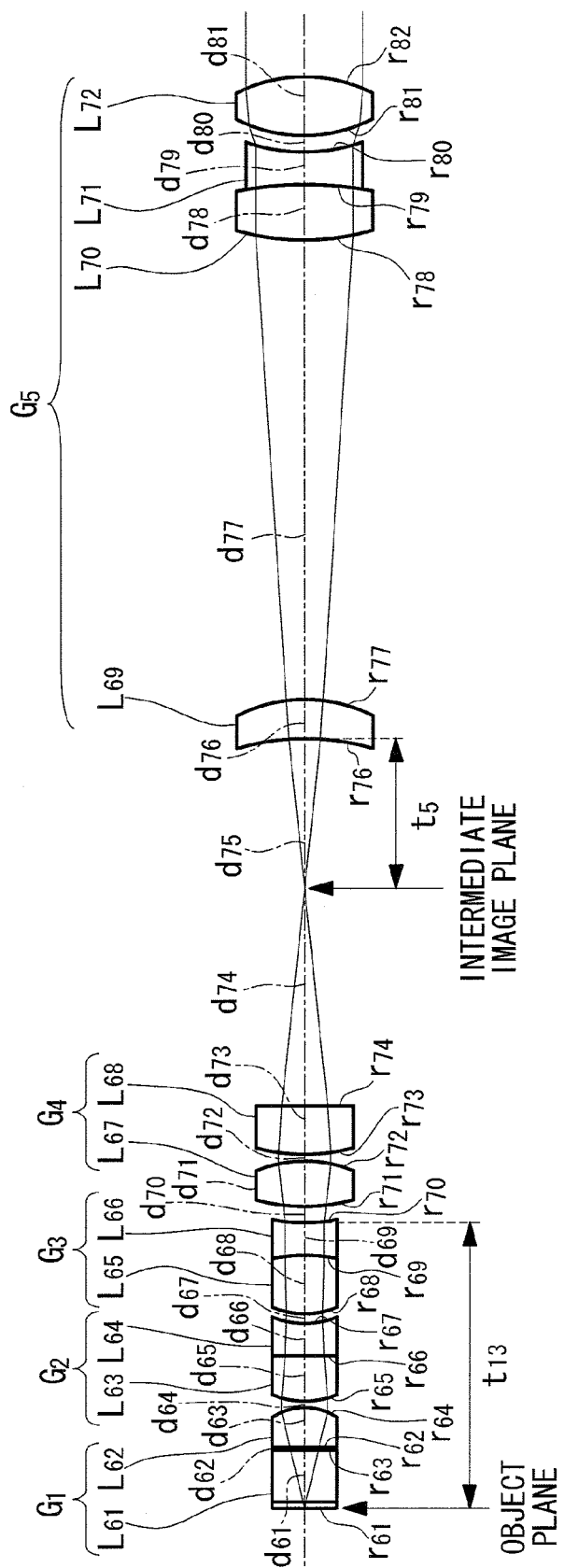
FIG. 6 is a diagram showing the structure of an objective optical system according to a third embodiment of the present invention.
Figure 7:
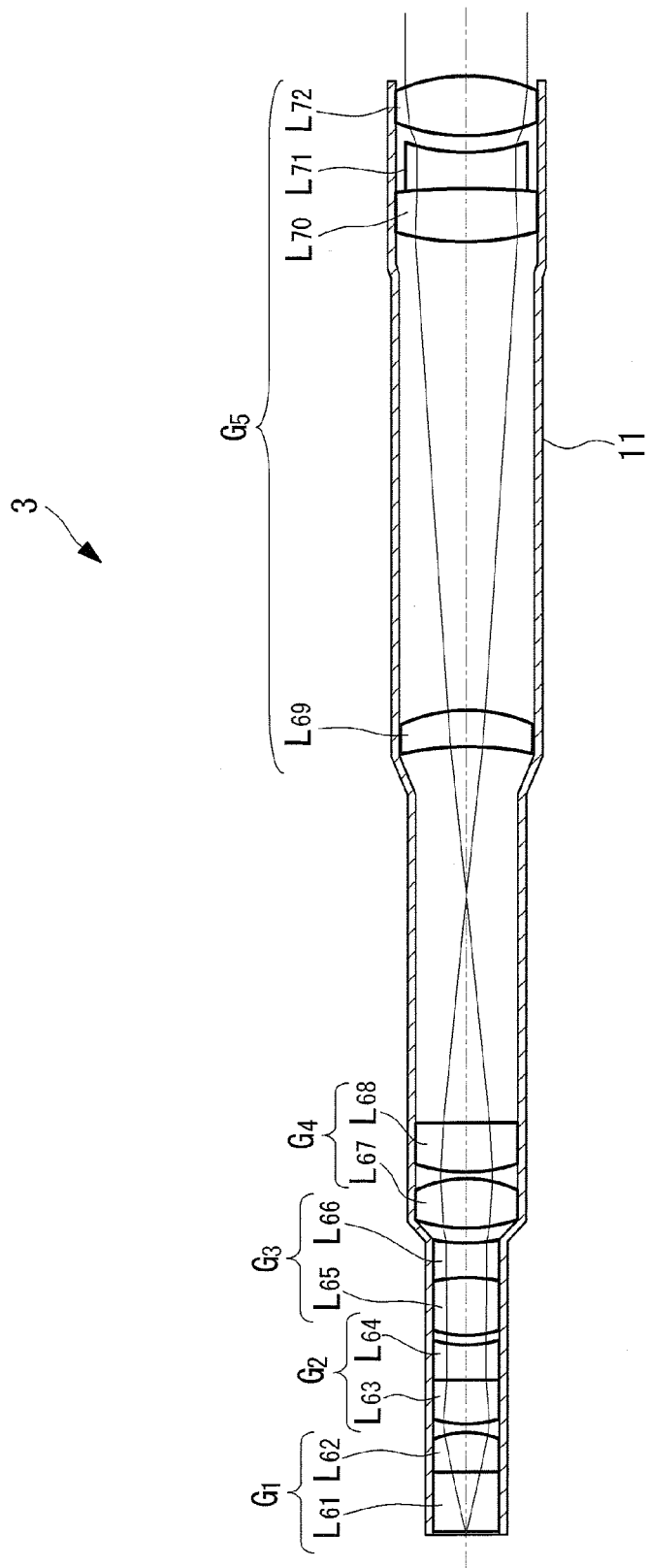
FIG. 7 is a diagram showing the structure of the objective optical system in FIG. 6, including an outer cylinder.

The objective optical system 3 according to this embodiment is an immersion objective optical system designed to focus at infinity and having an intermediate image plane, as shown in FIGS. 6 and 7.

This objective optical system 3 includes a first lens group (first group) $G_1$ having positive refractive power, including a lens disposed on the extreme object side, whose object-side lens surface is substantially flat, and a convex lens with the convex surface facing towards the image side; a second lens group (second group) $G_2$ having positive refractive power, whose extreme-object-side lens surface is a convex surface facing towards the object side; a third lens group (third group) $G_3$ having negative refractive power, whose extreme-image-side lens surface is a concave surface facing towards the image side; a fourth lens group (fourth group) $G_4$ having positive refractive power, whose image-side lens surface of the lens disposed on the extreme object side is a convex surface facing towards the image side and whose object-side lens surface of the lens disposed on the extreme image side is a convex surface facing towards the object side; a fifth lens group (fifth group) $G_5$ having positive refractive power including a lens whose surface closest to an intermediate image plane is a concave surface facing towards the intermediate image plane and a combined lens consisting of a convex lens and a concave lens and having negative refractive power at the joined surface; and the intermediate image plane disposed between the fourth lens group $G_4$ and the fifth lens group $G_5$.

More specifically, the first lens group $G_1$ having positive refractive power includes a first lens $L_{61}$ consisting of a parallel plate and a second lens $L_{62}$ consisting of a plano-convex lens with the convex surface facing towards the image plane side and having a d-line refractive index of 1.883.

The second lens group $G_2$ having positive refractive power includes a combined lens formed by joining a third lens $L_{63}$ consisting of a convex lens whose object-side surface is a convex surface facing towards the object side and a fourth lens $L_{64}$ consisting of a concave lens.

The third lens group $G_3$ having negative refractive power includes a combined lens formed by joining a fifth lens $L_{65}$ consisting of a biconvex lens and a sixth lens $L_{66}$ consisting of a biconcave lens whose image-side surface is a concave surface facing towards the image plane side.

The fourth lens group $G_4$ having positive refractive power as a whole includes a seventh lens $L_{67}$ consisting of a biconvex lens disposed on the extreme object side, whose image-side lens surface is a convex surface facing towards the image side and an eighth lens $L_{68}$ consisting of a plano-convex lens disposed on the extreme image side, whose object-side lens surface is a convex surface facing towards the object side.

The fifth lens group $G_5$ includes a ninth lens $L_{69}$ consisting of a meniscus lens whose lens surface closest to the intermediate image plane is a concave surface facing towards the intermediate image plane.

The fifth lens group $G_5$ having positive refractive power includes a combined lens formed by joining a tenth lens $L_{70}$ consisting of a biconvex lens and an eleventh lens $L_{71}$ consisting of a biconcave lens, the combined lens having negative refractive power at the joined surface, and a twelfth lens $L_{72}$ consisting of a biconvex lens.

The image-side exit pupil is disposed at the image side 3.29 mm away from the twelfth lens $L_{72}$.

In this embodiment, the respective lenses are configured to satisfy the following conditional expressions (6) to (11).

$0.28<(t_5 \cdot R_5)/(Dep \cdot FOV)<0.55$ (6)

$0.37<F_{12}/(t_{13} \cdot NA)<0.45$ (7)

$2.0<\phi_5/\phi_{12}<2.5$ (8)

$1.75<n_{12}<1.90$ (9)

$0.27<\Delta n_5<0.45$ (10)

$30<\Delta v_5<55$ (11)

where $F_{12}$ is the combined focal length of the first lens group $G_1$ and the second lens group $G_2$, $t_{13}$ is the optical axis length from the object plane to the surface on the extreme image side of the third lens group $G_3$, NA is the numerical aperture of the objective optical system 3 on the object side, $t_5$ is the distance from the intermediate image plane to the surface, in the fifth lens group $G_5$, closest to the intermediate image plane, $R_5$ is the radius of curvature of the surface, in the fifth lens group $G_5$, closest to the intermediate image plane, and Dep is the depth of focus on one side at the intermediate image plane, defined by the following expression.

$$Dep=\lambda/(NA/\beta)^2$$

where $\lambda$ is the wavelength of the d line (587.6 nm), and $\beta$ is the magnification from the object plane to the intermediate image plane.

FOV is the field of view on the object side of this immersion objective optical system, $\phi_5$ is the diameter of the largest lens among the lenses in the fifth lens group $G_5$, $\phi_{12}$ is the diameter of the smallest lens among the lenses in the first lens group $G_1$ and the second lens group $G_2$, $n_{12}$ is the largest refractive index (d line) of the lenses in the first lens group $G_1$ and the second lens group $G_2$, $\Delta n_5$ is the difference in refractive index of the combined lens having the joined surface with negative refractive power in the fifth lens group $G_5$ (d line), and $\Delta v_5$ is the difference in Abbe number of the combined lens having the joined surface with negative refractive power in the fifth lens group $G_5$ (d line).

An increase in the field of view causes field curvature. To correct such field curvature, conditional expression (6) defines the proper relationship of the field of view, FOV, on the object side of the objective optical system of the present invention, the radius of curvature, $R_5$, of the lens in the fifth lens group $G_5$ whose lens surface closest to the intermediate image plane is a concave surface facing towards the intermediate image plane, the distance, $t_5$, between the lens surface, in the fifth lens group $G_5$, closest to the intermediate image plane and the intermediate image plane, and the depth of focus at the intermediate image plane, Dep.

If conditional expression (6) is smaller than 0.28, $t_5$ decreases. A decreased $t_5$ requires a reduction in radius of curvature $R_5$ to bend a beam at a low beam height. A reduction in $R_5$ results in over-correction of field curvature, which is inconvenient. An increase in the field of view FOV is also inconvenient because it makes correction of field curvature difficult.

In contrast, if conditional expression (6) is larger than 0.55, $t_5$ increases. This conversely increases the radius of curvature $R_5$, making correction of field curvature impossible, which is inconvenient.

Furthermore, it is preferable that expression (6) fall within the following range to correct aberrations.

$$0.4<(t_5 \cdot R_5)/(Dep \cdot FOV)<0.55$$

Accordingly, by satisfying conditional expression (6), it is possible to provide an objective optical system that has a small outside diameter and a wide field of view, can excellently correct various aberrations, has such a high numerical aperture that it can be used for two-photon excitation, and is suited for in vivo observation.

Conditional expression (7) defines the preferable relationship of the combined focal length, $F_{12}$, of the first lens group $G_1$ and the second lens group $G_2$, the optical axis length, $t_{13}$, from the object plane to the surface on the extreme image side of the third lens group $G_3$, and the object-side numerical aperture, NA, to correct aberrations resulting from a reduction in diameter of the tip.

If conditional expression (7) is smaller than 0.37, the combined focal length, $F_{12}$, of the first lens group $G_1$ and the second lens group $G_2$ decreases, which increases the refractive power of the first lens group $G_1$ and the second lens group $G_2$. This causes severe spherical aberration, making correction thereof difficult. Furthermore, an increase in object-side numerical aperture, NA, causes severe spherical aberration, making correction thereof difficult.

In contrast, if conditional expression (7) is larger than 0.45, the combined focal length, $F_{12}$, of the first lens group $G_1$ and the second lens group $G_2$ increases, which decreases the refractive power. As a result, an inconvenience, such as over-correction of spherical aberration, occurs. Otherwise, a decrease in object-side numerical aperture, NA, causes over-correction of aberration, such as spherical aberration, which is inconvenient.

In order to reduce the diameter of the tip, the diverging light from the specimen surface has to be converted into substantially converging light before it spreads too much, which causes severe aberration (mainly spherical aberration) at the small diameter portion at the tip. Therefore, the aberration caused at the tip has to be corrected by increasing the beam diameter in the fifth lens group $G_5$. Thus, conditional expression (8) defines the relationship between the outside diameter of the smallest lens in the first and second groups and the outside diameter of the largest lens in the fifth lens group $G_5$.

If conditional expression (8) is smaller than 2.0, the diameter, $\phi_5$, of the largest lens among the lenses in the fifth lens group $G_5$ decreases. This makes it difficult to correct, in the fifth lens group $G_5$, various aberrations, such as spherical aberration, caused in the first lens group $G_1$ to the fourth lens group $G_4$.

In contrast, if conditional expression (8) is larger than 2.5, the diameter, $\phi_5$, of the largest lens among the lenses in the fifth lens group $G_5$ increases, and the diameter, $\phi_{12}$, of the smallest lens among the lenses in the first lens group $G_1$ and the second lens group $G_2$ decreases. This causes over-correction, in the fifth lens group $G_5$, of various aberrations, such as spherical aberration, caused in the first lens group $G_1$ to the fourth lens group $G_4$.

Regarding conditional expression (9), although the refractive power of the first lens group $G_1$ and the second lens group $G_2$ at the tip portion has to be increased to reduce the diameter of the tip, it is preferable that the largest refractive index among the lenses in the first lens group $G_1$ and the second lens group $G_2$ be set to a proper value to correct aberrations.

If conditional expression (9) is smaller than 1.75, the radii of curvatures of the first and second lens groups $G_1$ and $G_2$ decrease. This results in under-correction of spherical aberration and causes field curvature, which is inconvenient.

In contrast, if conditional expression (9) is larger than 1.90, the radii of curvatures of the first and second lens groups $G_1$ and $G_2$ increase. This results in over-correction of spherical aberration and field curvature, which is inconvenient.

Conditional expression (10) defines the difference in refractive index (d line), $\Delta n_5$, of the combined lens having the joined surface with negative refractive power in the fifth lens group $G_5$ to correct aberrations, such as spherical aberration, caused in the first lens group $G_1$ to the fourth lens group $G_4$.

If conditional expression (10) is smaller than 0.27, the difference in refractive index at the joined surface having negative refractive power decreases, making it difficult to correct aberrations, such as spherical aberration, caused in the first lens group $G_1$ to the fourth lens group $G_4$.

In contrast, if conditional expression (10) is larger than 0.45, the difference in refractive index at the joined surface having negative refractive power increases, resulting in an inconvenience such as over-correction of aberrations or an increase in beam height.

Conditional expression (11) defines the difference in Abbe number (d line), $\Delta v_5$, of the combined lens having the joined surface with negative refractive power in the fifth lens group $G_5$ to correct chromatic aberration caused in the first lens group $G_1$ to the fourth lens group $G_4$.

If conditional expression (11) is smaller than 30, chromatic aberration is under-corrected.

In contrast, if conditional expression (11) is larger than 55, the chromatic aberration is over-corrected, which is inconvenient.

Therefore, by satisfying conditional expressions (7) to (11), various aberrations caused in these lens groups, such as spherical aberration, field curvature, and chromatic aberration, can be properly corrected.

Figure 10:
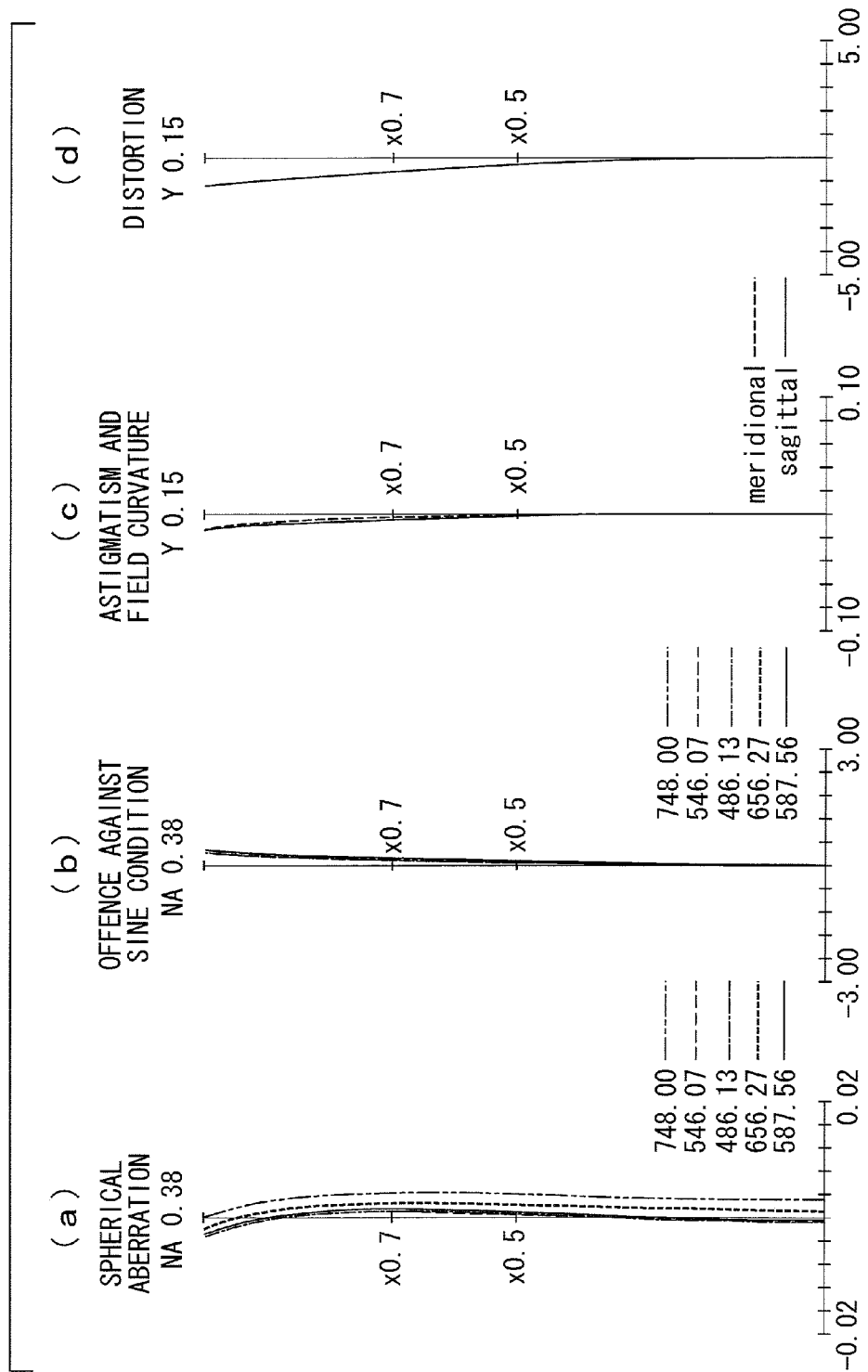
FIG. 10 contains aberration diagrams of the example of the objective optical system in FIG. 6, showing (a) spherical aberration, (b) the offence against the sine condition, (c) astigmatism and field curvature, and (d) distortion.

Table 4 shows the lens data of an example of the objective optical system 3 according to this embodiment. FIG. 6 shows a ray diagram of this example, and FIG. 10 shows aberration diagrams.

TABLE 4

| SURFACE NO. | r | d | nd | vd | EFFECTIVE DIAMETER |
|---|---|---|---|---|---|
| OBJECT PLANE | ∞ | 0.05 (WORKING DISTANCE) | 1.333 (WATER) | 55 | |
| 61 | ∞ | 0.77 | 1.883 | 40.8 | 0.6 |
| 62 | ∞ | 0.03 | | | 0.6 |
| 63 | ∞ | 0.5 | 1.883 | 40.8 | 0.6 |
| 64 | −0.915 | 0.1 | | | 0.6 |
| 65 | 1.06 | 0.6 | 1.6779 | 55.3 | 0.6 |
| 66 | ∞ | 0.45 | 1.6779 | 55.3 | 0.6 |
| 67 | 9.777 | 0.15 | | | 0.6 |
| 68 | 1.628 | 0.75 | 1.43875 | 94.9 | 0.6 |
| 69 | −1.628 | 0.45 | 1.6779 | 55.3 | 0.6 |
| 70 | 1.628 | 0.22 | | | 0.6 |
| 71 | 2.744 | 0.64 | 1.48749 | 70.2 | 1 |
| 72 | −1.462 | 0.08 | | | 1 |
| 73 | 2.551 | 0.65 | 1.6779 | 55.3 | 1 |
| 74 | ∞ | 3 | | | 1 |
| 75 (IMAGE PLANE) | ∞ | 2 | | | |
| 76 | −3.423 | 0.5 | 1.6779 | 55.3 | 1.6 |
| 77 | −2.167 | 6.2 | | | 1.6 |
| 78 | 3.32 | 0.7 | 1.43875 | 94.9 | 1.6 |
| 79 | −7.288 | 0.47 | 1.883 | 40.8 | 1.6 |
| 80 | 2.025 | 0.23 | | | 1.6 |
| 81 | 2.417 | 0.75 | 1.48749 | 70.2 | 1.6 |
| 82 | −2.417 | 3.29 | | | 1.6 |
| 83 (PUPIL POSITION) | ∞ | | | | |

In the example, the values in conditional expressions (6) to (11) are as follows:

$F_{12}=0.63$ $t_{13}=3.87$ $NA=0.38$ $\phi_{12}=0.8$ $\phi_5=1.8$ $t_5=2.0$ $R_5=3.423$ $Dep=54.7$ $\beta=3.67$ $FOV=0.3$ Therefore, the following hold:

$(t_5 \cdot R_5)/(Dep \cdot FOV)=0.42$ \hfill (6)

$F_{12}/(t_{13} \cdot NA)=0.43$ \hfill (7)

$\phi_5/\phi_{12}=2.3$ \hfill (8)

$n_{12}=1.88$ \hfill (9)

$\Delta n_5=0.44$ \hfill (10)

$\Delta v_5=54.1$ \hfill (11)

As shown in FIG. 7, in the objective optical system 3 of this example, the lenses $L_{61}$ to $L_6$6 have a maximum diameter of 0.8 mm (the effective diameter is 0.6 mm), the lenses $L_{67}$ and $L_{68}$ have a maximum diameter of 1.2 mm (the effective diameter is 1.0 mm), and the lenses $L_{69}$ to $L_{73}$ have a maximum diameter of 1.8 mm (the effective diameter is 1.6 mm). The tip portion, i.e., from the lenses $L_{61}$ to $L_{66}$, consists only of the lenses having a very small diameter. This allows an outer cylinder 11 accommodating these lenses $L_{61}$ to $L_{72}$, in particular, the lenses $L_{61}$ to $L_{66}$ in the first to third lens groups $G_1$ to $G_3$, to be made extremely thin. Therefore, this is suitable for performing in vivo observation over a wide area of a deep part of the body of a small laboratory animal, such as a mouse, in a minimally invasive manner for a relatively long time. Furthermore, in the above-described invention, the average inside diameter of the outer cylinder may be 1 mm or less. Herein, the outer cylinder that holds the objective optical system of the present invention is much thinner and longer than that of the conventional one, and it may have, for example, an outside diameter of about 2 mm or less (a lens diameter of 1.8 mm or less) and a length of about 20 mm or more (in the Table, 22.53 mm). That is, in a thin, long shape in which the dimensional ratio of the outside diameter to the length is 1:10 or more at a portion where the objective optical system is arranged in series along the optical axis, the present invention can provide an objective lens having a wider field of view than the conventional objective lens. This enables most advantageous microscopic observation of an object in an observation field that requires the above-described dimensional ratio. In addition, regardless of the presence or absence of the outer cylinder, this is suitable for use in arbitrary small apparatuses that allow only an installation space with the above-described dimensional ratio.

Furthermore, this example excellently corrects not only aberration for visible light, but also aberration for light in the near-infrared region. Thus, it is possible to observe not only the surface of a specimen, but also the inside of the living body using near-infrared light with relatively little influence by diffusion. In addition, because the object-side numerical aperture is relatively large, it can also be used for multiphoton excitation. Moreover, the present invention satisfies both a large FOV (wide field of view) and a high numerical aperture (high resolution), which are required for in vivo observation. The objective optical system employing the present invention has, for example, a field of view on the object side of 0.25 or more, an object-side numerical aperture of 0.35 or more, and a tip lens diameter of 0.9 mm or less, and a lens barrel from the tip has an outside diameter of substantially 1 mm or less.

The symbols in the table are as follows:

r: radius of curvature, d: distance between surfaces, nd: refractive index (d line), vd: Abbe number (d line). The unit of length is mm.

Fourth Embodiment

Next, an objective optical system 4 according to a fourth embodiment of the present invention will be described with reference to the drawings.

Figure 8:
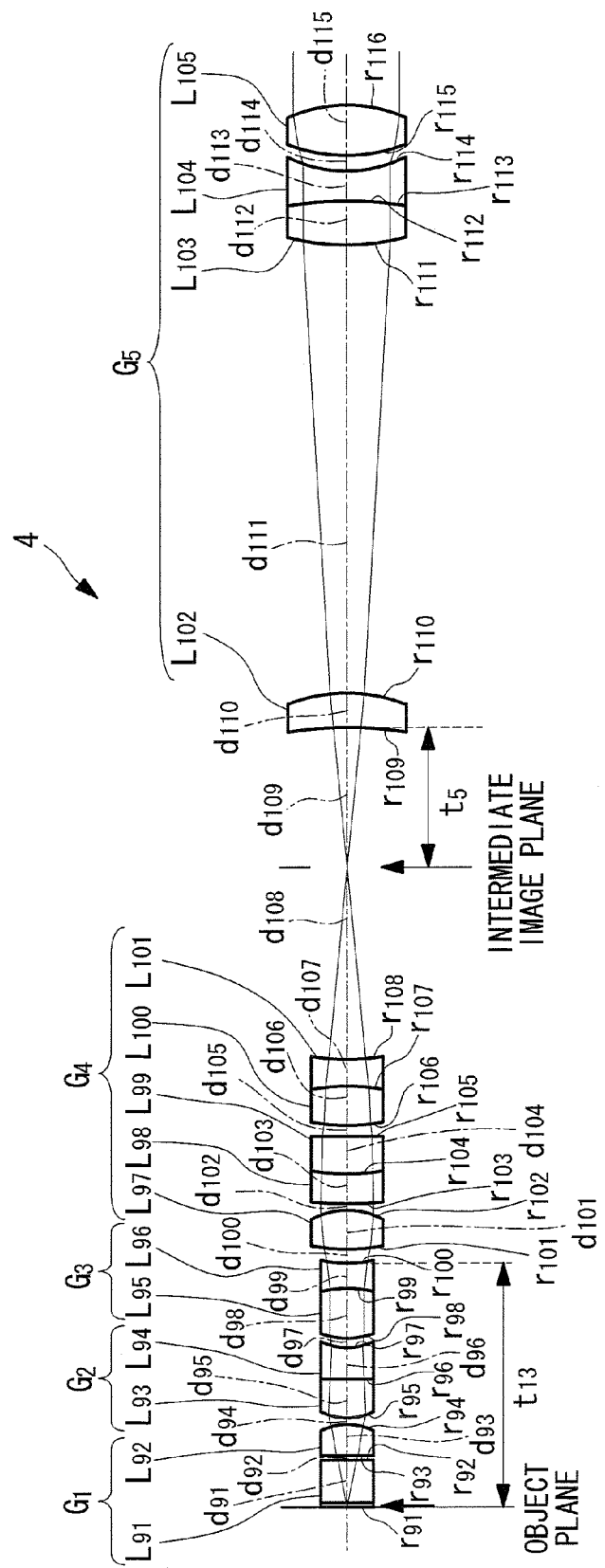
FIG. 8 is a diagram showing the structure of an objective optical system according to a fourth embodiment of the present invention.

As shown in FIG. 8, the objective optical system 4 according to this embodiment is designed to focus at infinity and has an intermediate image plane.

This objective optical system 4 includes a first lens group $G_1$ having positive refractive power, including a lens disposed on the extreme object side, whose object-side lens surface is substantially flat, and a plano-convex lens with the convex surface facing towards the image side; a second lens group $G_2$ having positive refractive power, whose extreme-object-side lens surface is a convex surface facing towards the object side; a third lens group $G_3$ having negative refractive power, whose extreme-image-side lens surface is a concave surface facing towards the image side; a fourth lens group $G_4$ having positive refractive power, whose image-side lens surface of the lens disposed on the extreme object side is a convex surface facing towards the image side and whose object-side lens surface of the lens disposed on the extreme image side is a convex surface facing towards the object side; a fifth lens group $G_5$ having positive refractive power including a lens whose surface closest to an intermediate image plane is a concave surface facing towards the intermediate image plane and a combined lens consisting of a convex lens and a concave lens and having negative refractive power at the joined surface; and the intermediate image plane disposed between the fourth lens group $G_4$ and the fifth lens group $G_5$.

More specifically, the first lens group $G_1$ having positive refractive power includes a first lens $L_{91}$ consisting of a parallel plate and a second lens $L_{92}$ consisting of a plano-convex lens with the convex surface facing towards the image plane side and having a d-line refractive index of 1.883.

The second lens group $G_2$ having positive refractive power includes a combined lens formed by joining a third lens $L_{93}$ consisting of a biconvex lens whose object-side surface is a convex surface facing towards the object side and a fourth lens $L_{94}$ consisting of a plano-convex lens.

The third lens group $G_3$ having negative refractive power includes a combined lens formed by joining a fifth lens $L_{95}$ consisting of a biconvex lens and a sixth lens $L_{96}$ consisting of a biconcave lens whose image-side surface is a concave surface facing towards the image plane side.

The fourth lens group $G_4$ having positive refractive power as a whole includes a seventh lens $L_{97}$ consisting of a biconvex lens disposed on the extreme object side, whose image-side lens surface is a convex surface facing towards the image side, a combined lens formed by joining an eighth lens $L_{98}$ and a ninth lens $L_{99}$, whose object-side lens surface is a convex surface facing towards the object side, and a combined lens disposed on the extreme image side and formed by joining a tenth lens $L_{100}$ and an eleventh lens $L_{101}$, whose object-side lens surface is a convex surface facing towards the object side.

The fifth lens group $G_5$ includes a twelfth lens $L_{102}$ consisting of a meniscus lens whose lens surface closest to the intermediate image plane is a concave surface facing towards the intermediate image plane.

The fifth lens group $G_5$ having positive refractive power includes a combined lens formed by joining a thirteenth lens $L_{103}$ consisting of a biconvex lens and a fourteenth lens $L_{104}$ consisting of a biconcave lens, the combined lens having negative refractive power at the joined surface, and a fifteenth lens $L_{105}$ consisting of a biconvex lens.

The image-side exit pupil is disposed at the image side 3.56 mm away from the fifteenth lens $L_{105}$.

In this embodiment, the respective lenses are configured to satisfy the following conditional expressions (6) to (11).

$$0.28 < (t_5 \cdot R_5)/(Dep \cdot FOV) < 0.55 \quad (6)$$

$$0.37 < F_{12}/(t_{13} \cdot NA) < 0.45 \quad (7)$$

$$2.0 < \phi_5/\phi_{12} < 2.5 \quad (8)$$

$$1.75 < n_{12} < 1.90 \quad (9)$$

$$0.27 < \Delta n_5 < 0.45 \quad (10)$$

$$30 < \Delta v_5 < 55 \quad (11)$$

where $F_{12}$ is the combined focal length of the first lens group $G_1$ and the second lens group $G_2$, $t_{13}$ is the optical axis length from the object plane to the surface on the extreme image side of the third lens group $G_3$, NA is the object-side numerical aperture, $t_5$ is the distance from the intermediate image plane to the surface, in the fifth lens group $G_5$, closest to the intermediate image plane, $R_5$ is the radius of curvature of the surface, in the fifth lens group $G_5$, closest to the intermediate image plane, and Dep is the depth of focus on one side at the intermediate image plane, defined by the following expression.

$$Dep = \lambda/(NA/\beta)^2$$

where $\lambda$ is the wavelength of the d line (587.6 nm), and $\beta$ is the magnification from the object plane to the intermediate image plane.

FOV is the field of view on the object side, $\phi_5$ is the diameter of the largest lens among the lenses in the fifth lens group $G_5$, $\phi_{12}$ is the diameter of the smallest lens among the lenses in the first lens group $G_1$ and the second lens group $G_2$, $n_{12}$ is the largest refractive index (d line) of the lenses in the first lens group $G_1$ and the second lens group $G_2$, $\Delta n_5$ is the difference in refractive index of the combined lens having the joined surface with negative refractive power in the fifth lens group $G_5$ (d line), and $\Delta v_5$ is the difference in Abbe number of the combined lens having the joined surface with negative refractive power in the fifth lens group $G_5$ (d line).

Figure 11:
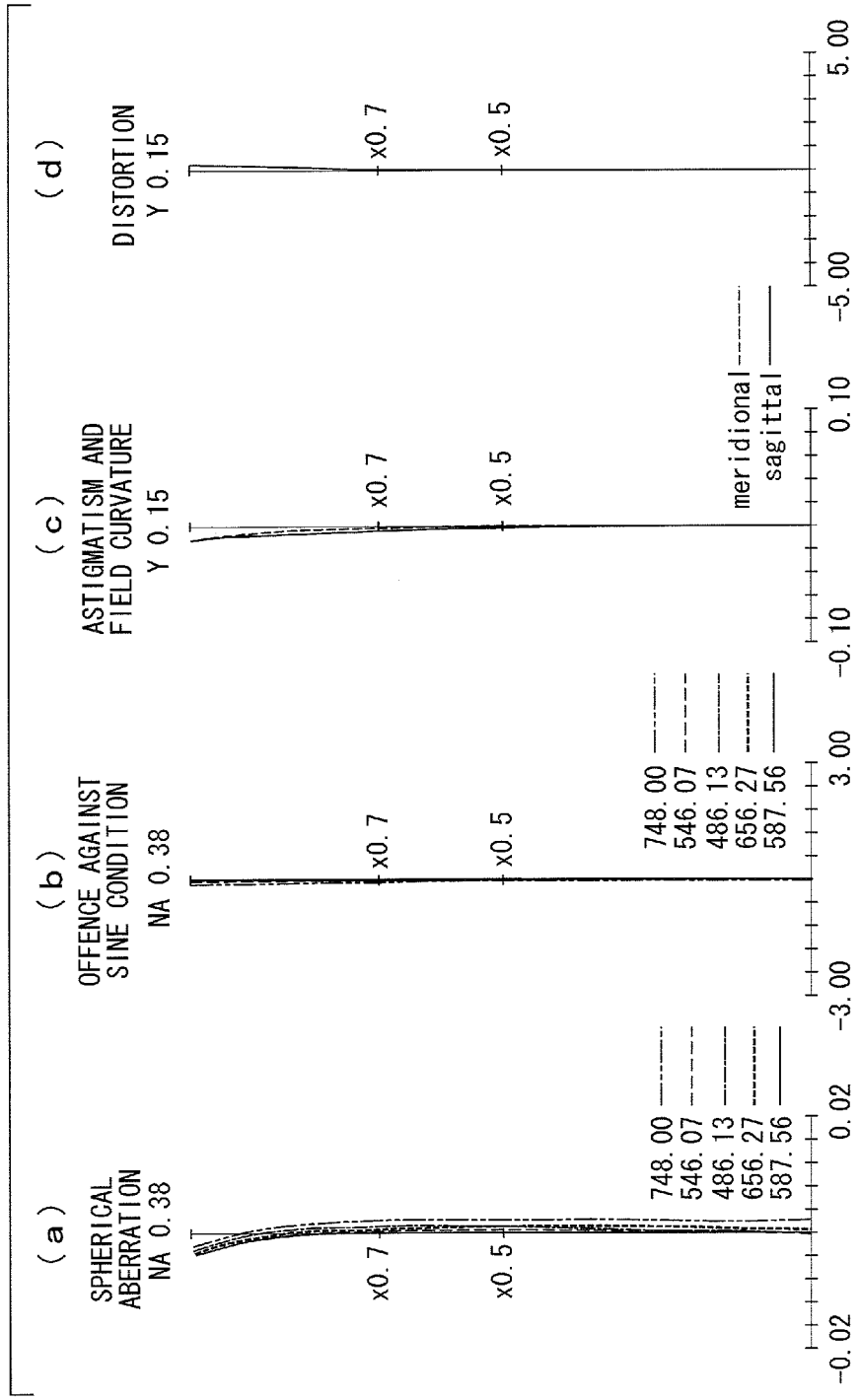
FIG. 11 contains aberration diagrams of the example of the objective optical system in FIG. 8, showing (a) spherical aberration, (b) the offence against the sine condition, (c) astigmatism and field curvature, and (d) distortion.

Table 5 shows the lens data of an example of the objective optical system 4 according to this embodiment. FIG. 8 shows a ray diagram of this example, and FIG. 11 shows aberration diagrams.

TABLE 5

| SURFACE NO. | r | d | nd | vd | EFFECTIVE DIAMETER |
|---|---|---|---|---|---|
| OBJECT PLANE | ∞ | 0.05 (WORKING DISTANCE) | 1.333 (WATER) | 55 | |
| 91 | ∞ | 0.66 | 1.883 | 40.8 | 0.6 |
| 92 | ∞ | 0.03 | | | 0.6 |
| 93 | ∞ | 0.5 | 1.883 | 40.8 | 0.6 |
| 94 | −0.942 | 0.1 | | | 0.6 |
| 95 | 0.856 | 0.6 | 1.678 | 55.3 | 0.6 |
| 96 | ∞ | 0.45 | 1.773 | 49.6 | 0.6 |
| 97 | 0.74 | 0.15 | | | 0.6 |
| 98 | 1.522 | 0.75 | 1.487 | 70.2 | 0.6 |
| 99 | −1.522 | 0.35 | 1.678 | 55.3 | 0.6 |
| 100 | 1.522 | 0.2 | | | 0.6 |
| 101 | 2.385 | 0.6 | 1.439 | 94.9 | 1 |
| 102 | −1.072 | 0.1 | | | 1 |
| 103 | 6.2 | 0.45 | 1.487 | 70.2 | 1 |
| 104 | 3.3 | 0.57 | 1.678 | 55.3 | 1 |
| 105 | ∞ | 0.15 | | | 1 |
| 106 | 4.133 | 0.57 | 1.773 | 49.6 | 1 |

TABLE 5-continued

| SURFACE NO. | r | d | nd | vd | EFFECTIVE DIAMETER |
|---|---|---|---|---|---|
| 107 | −4.133 | 0.41 | 1.613 | 44.3 | 1 |
| 108 | 4.133 | 2.9 | | | 1 |
| 109 (IMAGE PLANE) | ∞ | 2.1 | | | |
| 110 | −4.901 | 0.5 | 1.678 | 55.3 | 1.6 |
| 111 | −2.681 | 6.69 | | | 1.6 |
| 112 | 3.626 | 0.6 | 1.439 | 94.9 | 1.6 |
| 113 | −11.096 | 0.47 | 1.883 | 40.8 | 1.6 |
| 114 | 2.025 | 0.23 | | | 1.6 |
| 115 | 2.461 | 0.74 | 1.487 | 70.2 | 1.6 |
| 116 | −2.461 | 3.56 | | | 1.6 |
| 117 (PUPIL POSITION) | ∞ | | | | |

In this example, the values in conditional expressions (6) to (11) are as follows:

$F_{12}=0.56$ $t_{13}=3.66$ $NA=0.38$ $\phi_{12}=0.8$ $\phi_5=1.8$ $t_5=2.1$ $R_5=4.901$ $Dep=64.7$ $\beta=3.99$ $FOV=0.3$ Therefore, the following hold:

$(t_5 \cdot R_5)/(Dep \cdot FOV)=0.53$ (6)

$F_{12}/(t_{13} \cdot NA)=0.4$ (7)

$\phi_5/\phi_{12}=2.3$ (8)

$n_{12}=1.88$ (9)

$\Delta n_5=0.44$ (10)

$\Delta v_5=54.1$ (11)

Although the objective optical system 4 according to this embodiment is basically the same as that according to the third embodiment, this is an example in which spherical aberration, axial chromatic aberration, and coma are corrected and axial image-forming performance is further improved compared to the third embodiment.

In the objective optical system 4 according to this embodiment, the lenses $L_{91}$ to $L_{96}$ have a maximum diameter of 0.8 mm, the lenses $L_{97}$ to $L_{101}$ have a maximum diameter of 1.2 mm, and the lenses $L_{102}$ to $L_{105}$ have a maximum diameter of 1.8 mm. The tip portion, i.e., from the lenses $L_{91}$ to $L_{96}$, consists only of the lenses having a very small diameter. Therefore, this is suitable for performing in vivo observation over a wide area of a deep part of the body of a small laboratory animal, such as a mouse, in a minimally invasive manner for a relatively long time.

Herein, the outer cylinder that holds the objective optical system of the present invention is much thinner and longer than the conventional one, and it may have, for example, an outside diameter of about 2 mm or less (a lens diameter of 1.8 mm or less) and a length of about 20 mm or more (in the Table, 24.43 mm). That is, in a thin, long shape in which the dimensional ratio of the outside diameter to the length is 1:10 or more at a portion where the objective optical system is arranged in series along the optical axis, the present invention can provide an objective lens having a wider field of view than the conventional objective optical system. This enables most advantageous microscopic observation of the object in the observation field that requires the above-described dimensional ratio. In addition, regardless of the presence or absence of the outer cylinder, this is suitable for use in arbitrary small apparatuses that allow only an installation space having the above-described dimensional ratio.

Furthermore, this embodiment corrects not only aberration for visible light, but also aberration for light in the near-infrared region. Thus, it is possible to observe not only the surface of a specimen, but also the inside of the living body using near-infrared light with relatively little influence by diffusion. In addition, because the object-side numerical aperture is relatively large, it can also be used for multiphoton excitation.

The symbols in the table are as follows:
r: radius of curvature, d: distance between surfaces, nd: refractive index (d line), vd: Abbe number (d line). The unit of length is mm.

Fifth Embodiment

Next, an objective optical system 5 according to a fifth embodiment of the present invention will be described below with reference to the drawings.

Figure 9:
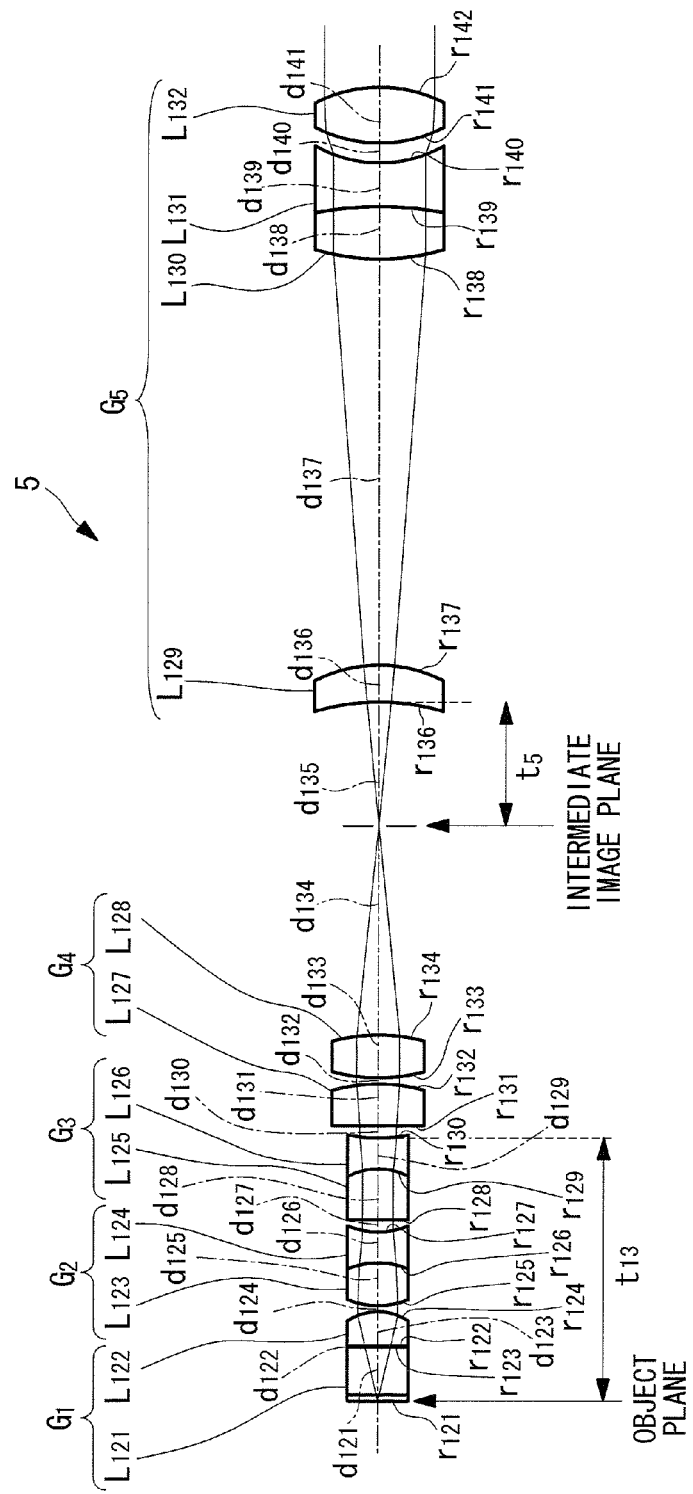
FIG. 9 is a diagram showing the structure of an objective optical system according to a fifth embodiment of the present invention.

As shown in FIG. 9, the objective optical system according to this embodiment is designed to focus at infinity and has an intermediate image plane.

The objective optical system 5 according to this embodiment includes a first lens group $G_1$ having positive refractive power, including a lens disposed on the extreme object side, whose object-side lens surface is substantially flat, and a plano-convex lens with the convex surface facing towards the image side; a second lens group $G_2$ having positive refractive power, whose extreme-object-side lens surface is a convex surface facing towards the object side; a third lens group $G_3$ having negative refractive power, whose extreme-image-side lens surface is a concave surface facing towards the image side; a fourth lens group $G_4$ having positive refractive power, whose image-side lens surface of the lens disposed on the extreme object side is a convex surface facing towards the image side and whose object-side lens surface of the lens disposed on the extreme image side is a convex surface facing towards the object side; a fifth lens group $G_5$ having positive refractive power including a lens whose surface closest to the intermediate image plane is a concave surface facing towards the intermediate image plane and a combined lens consisting of a convex lens and a concave lens and having negative refractive power at the joined surface.

Also, an intermediate image plane is disposed between the fourth lens group $G_4$ and the fifth lens group $G_5$.

More specifically, the first lens group $G_1$ having positive refractive power includes a first lens $L_{121}$ consisting of a parallel plate and a second lens $L_{122}$ consisting of a plano-convex lens with the convex surface facing towards the image plane side and having a d-line refractive index of 1.773.

The second lens group $G_2$ having positive refractive power includes a combined lens formed by joining a third lens $L_{123}$ consisting of a biconvex lens whose object-side surface is a convex surface facing towards the object side and a fourth lens $L_{124}$ consisting of a plano-convex lens.

The third lens group $G_3$ having negative refractive power includes a combined lens formed by joining a fifth lens $L_{125}$ consisting of a biconvex lens and a sixth lens $L_{126}$ consisting of a biconcave lens whose image-side surface is a concave surface facing towards the image plane side.

The fourth lens group $G_4$ having positive refractive power as a whole includes a seventh lens $L_{127}$ consisting of a plano-convex lens disposed on the extreme object side, whose image-side lens surface is a convex surface facing towards the image side and an eighth lens $L_{128}$ consisting of a plano-convex lens disposed on the extreme image side, whose object-side lens surface is a convex surface facing towards the object side.

The fifth lens group $G_5$ includes a ninth lens $L_{129}$ consisting of a meniscus lens whose lens surface closest to the intermediate image plane is a concave surface facing towards the intermediate image plane.

The fifth lens group $G_5$ having positive refractive power includes a combined lens formed by joining a tenth lens $L_{130}$ consisting of a biconvex lens and an eleventh lens $L_{131}$ consisting of a biconcave lens, the combined lens having negative refractive power at the joined surface, and a twelfth lens $L_{132}$ consisting of a biconvex lens.

The image-side exit pupil is disposed at the image side 3.51 mm away from the twelfth lens $L_{132}$.

In this embodiment, the respective lenses are configured to satisfy the following conditional expressions (6) to (11).

$$0.28 < (t_5 \cdot R_5)/(Dep \cdot FOV) < 0.55 \quad (6)$$

$$0.37 < F_{12}/(t_{13} \cdot NA) < 0.45 \quad (7)$$

$$2.0 < \phi_5/\phi_{12} < 2.5 \quad (8)$$

$$1.75 < n_{12} < 1.90 \quad (9)$$

$$0.27 < \Delta n_5 < 0.45 \quad (10)$$

$$30 < \Delta v_5 < 55 \quad (11)$$

where $F_{12}$ is the combined focal length of the first lens group $G_1$ and the second lens group $G_2$, $t_{13}$ is the optical axis length from the object plane to the surface on the extreme image side of the third lens group $G_3$, NA is the object-side numerical aperture of this objective optical system 5, $t_5$ is the distance from the intermediate image plane to the surface, in the fifth lens group $G_5$, closest to the intermediate image plane, $R_5$ is the radius of curvature of the surface, in the fifth lens group $G_5$, closest to the intermediate image plane, and Dep is the depth of focus on one side at the intermediate image plane, defined by the following expression.

$$Dep = \lambda/(NA/\beta)^2$$

where $\lambda$ is the wavelength of the d line (587.6 nm), and $\beta$ is the magnification from the object plane to the intermediate image plane.

FOV is the field of view on the object side of this objective optical system, $\phi_5$ is the diameter of the largest lens among the lenses in the fifth lens group $G_5$, $\phi_{12}$ is the diameter of the smallest lens among the lenses in the first lens group $G_1$ and the second lens group $G_2$, $n_{12}$ is the largest refractive index (d line) of the lenses in the first lens group $G_1$ and the second lens group $G_2$, $\Delta n_5$ is the difference in refractive index (d line) of the combined lens having the joined surface with negative refractive power in the fifth lens group $G_5$, and $\Delta v_5$ is the difference in Abbe number (d line) of the combined lens having the joined surface with negative refractive power in the fifth lens group $G_5$.

Figure 12:
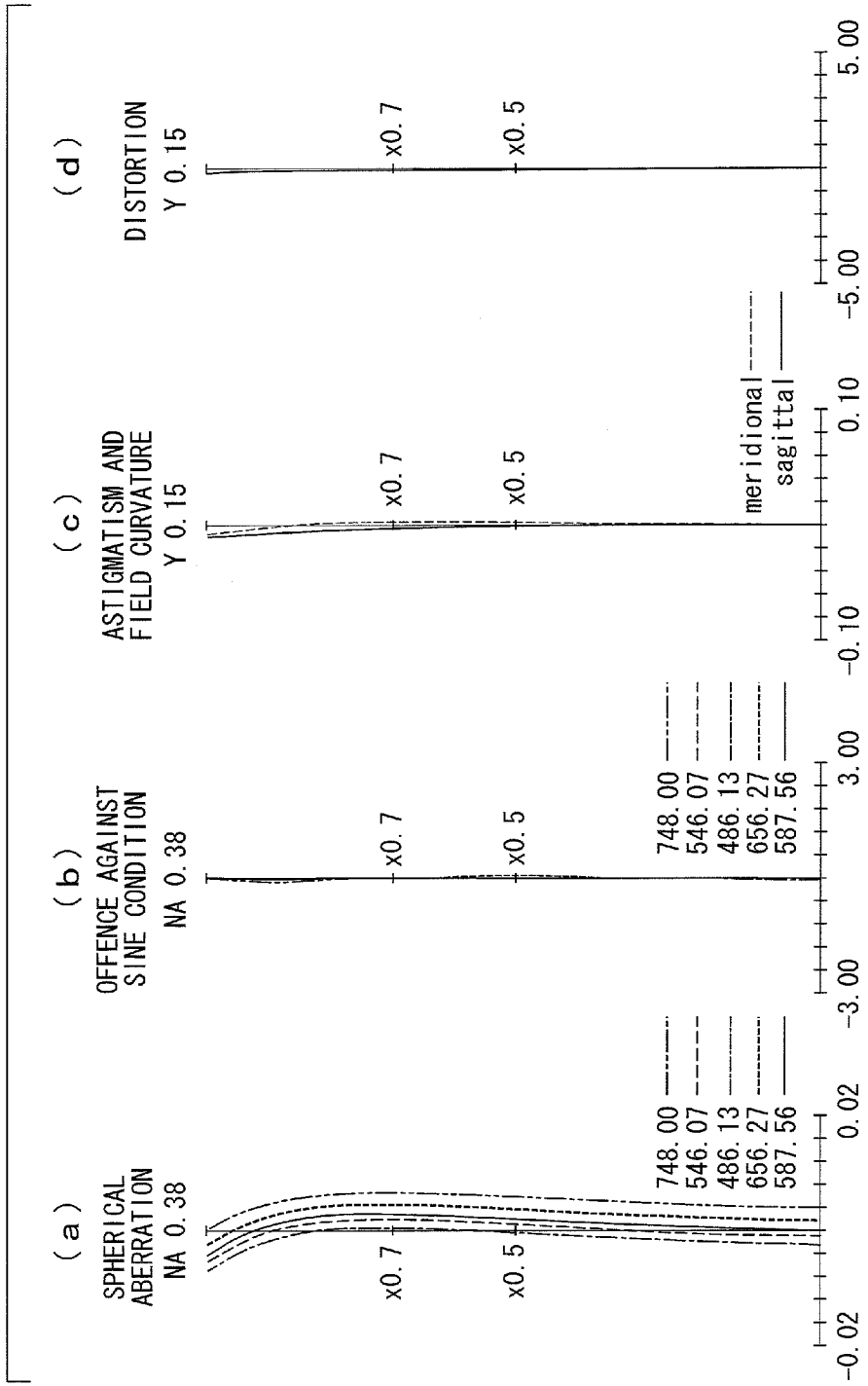
FIG. 12 contains aberration diagrams of the example of the objective optical system in FIG. 9, showing (a) spherical aberration, (b) the offence against the sine condition, (c) astigmatism and field curvature, and (d) distortion.

Table 6 shows the lens data of an example of the objective optical system 5 according to this embodiment. FIG. 9 shows a ray diagram of this example, and FIG. 12 shows aberration diagrams.

TABLE 6

| SURFACE NO. | r | d | nd | vd | EFFECTIVE DIAMETER |
|---|---|---|---|---|---|
| OBJECT PLANE | ∞ | 0.05 (WORKING DISTANCE) | 1.333 (WATER) | 55 | |
| 121 | ∞ | 0.65 | 1.773 | 49.6 | 0.6 |
| 122 | ∞ | 0.03 | | | 0.6 |
| 123 | ∞ | 0.5 | 1.773 | 49.6 | 0.6 |
| 124 | −0.806 | 0.1 | | | 0.6 |
| 125 | 1.007 | 0.6 | 1.773 | 49.6 | 0.6 |
| 126 | −0.95 | 0.43 | 1.613 | 44.3 | 0.6 |
| 127 | 0.661 | 0.15 | | | 0.6 |
| 128 | 2.965 | 0.7 | 1.439 | 94.9 | 0.6 |
| 129 | −0.858 | 0.45 | 1.613 | 44.3 | 0.6 |
| 130 | 2.17 | 0.15 | | | 0.6 |
| 131 | ∞ | 0.57 | 1.487 | 70.2 | 1.2 |
| 132 | −1.721 | 0.08 | | | 1.2 |
| 133 | 2.937 | 0.62 | 1.678 | 55.3 | 1.2 |
| 134 | −2.937 | 2.9 | | | 1.2 |
| 135 (IMAGE PLANE) | ∞ | 1.71 | | | |
| 136 | −2.989 | 0.6 | 1.487 | 70.2 | 1.6 |
| 137 | −2.001 | 5.5 | | | 1.6 |
| 138 | 3.127 | 0.8 | 1.497 | 81.5 | 1.6 |
| 139 | −2.159 | 0.5 | 1.773 | 49.6 | 1.6 |
| 140 | 1.801 | 0.23 | | | 1.6 |
| 141 | 2.234 | 0.8 | 1.487 | 70.2 | 1.6 |
| 142 | −2.234 | 3.51 | | | 1.6 |
| 143 (PUPIL POSITION) | ∞ | | | | |

In this example, the values in conditional expressions (6) to (11) are as follows:

$F_{12} = 0.55$ $t_{13} = 3.68$ $NA = 0.38$ $\phi_{12} = 0.8$ $\phi_5 = 1.8$ $t_5 = 1.71$ $R_5 = 2.989$ $Dep = 56.9$ $\beta = 3.74$ $FOV = 0.3$ Therefore, the following hold:

$$(t_5 \cdot R_5)/(Dep \cdot FOV) = 0.30 \quad (6)$$

$$F_{12}/(t_{13} \cdot NA) = 0.39 \quad (7)$$

$$\phi_5/\phi_{12} = 2.3 \quad (8)$$

$$n_{12} = 1.773 \quad (9)$$

$$\Delta n_5 = 0.276 \quad (10)$$

$$\Delta v_5 = 31.9 \quad (11)$$

Although the objective optical system 5 according to this embodiment is basically the same as that according to the third embodiment, this is an example in which distortion is corrected and image distortion is reduced compared to the third embodiment. In the objective optical system 5 according to this embodiment, the lenses $L_{121}$ to $L_{126}$ have a maximum diameter of 0.8 mm, the lenses $L_{127}$ and $L_{128}$ have a maximum diameter of 1.4 mm, the lenses $L_{129}$ to $L_{132}$ have a maximum diameter of 1.8 mm. The tip portion, i.e., from the lenses $L_{121}$ to $L_{126}$, consists only of the lenses having a very small diameter.

Therefore, this is suitable for performing in vivo observation over a wide area of a deep part of the body of a small laboratory animal, such as a mouse, in a minimally invasive manner for a relatively long time, with reduced image distortion.

Herein, the outer cylinder that holds the objective optical system of the present invention is much thinner and longer than the conventional one, and it may have, for example, an outside diameter of about 2 mm or less (a lens diameter of 1.8 mm or less) and a length of about 20 mm or more (in the Table, 21.58 mm). That is, in a thin, long shape in which the dimensional ratio of the outside diameter to the length is 1:10 or more at a portion where the objective optical system is arranged in series along the optical axis, the present invention can provide an objective lens having a wider field of view than the conventional objective optical system. This enables most advantageous microscopic observation of the object in the observation field that requires the above-described dimensional ratio. In addition, regardless of the presence or absence of the outer cylinder, this is suitable for use in arbitrary small apparatuses that allow only an installation space having the above-described dimensional ratio.

Furthermore, this embodiment corrects not only aberration for visible light, but also aberration for light in the near-infrared region. Thus, it is possible to observe not only the surface of a specimen, but also the inside of the living body using near-infrared light with relatively little influence by diffusion. In addition, because the object-side numerical aperture is relatively large, it can also be used for multiphoton excitation.

The symbols in the table are as follows:
r: radius of curvature, d: distance between surfaces, nd: refractive index (d line), vd: Abbe number (d line). The unit of length is mm.

Figure 13:
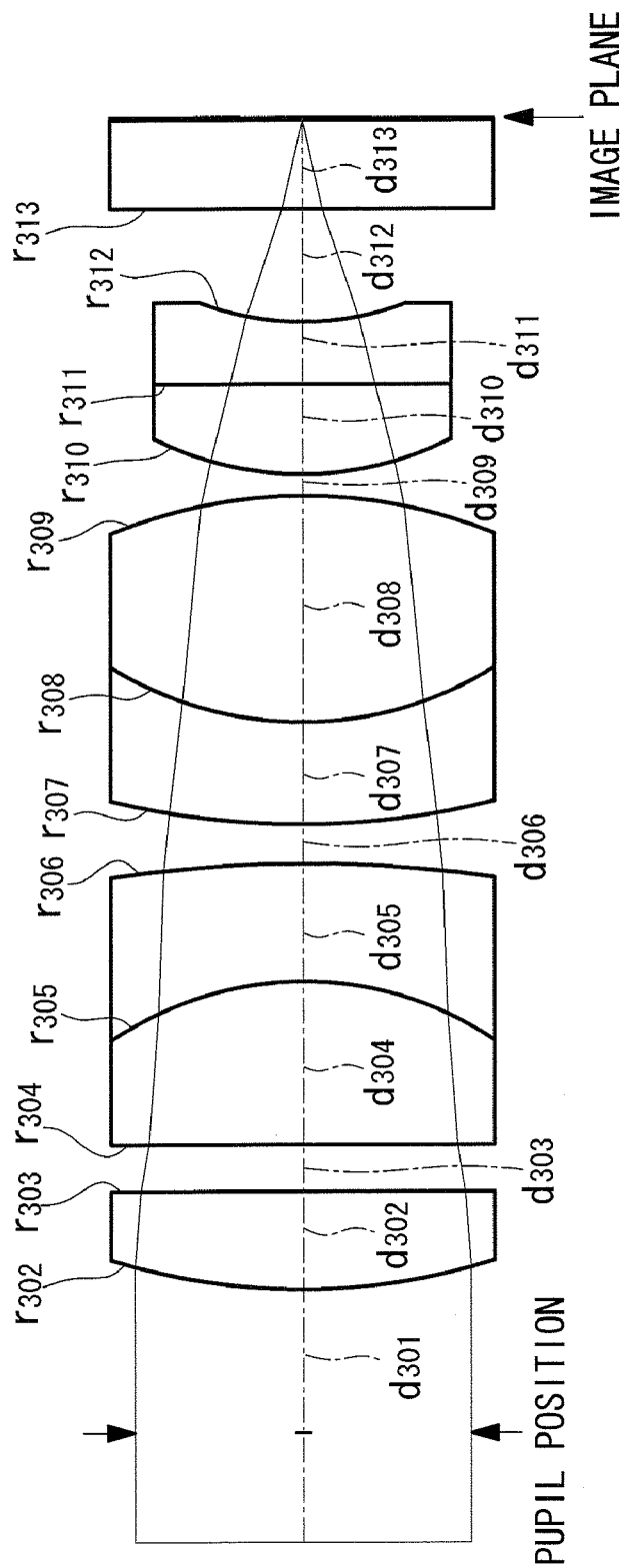
FIG. 13 is a diagram showing the structure of an another exemplary image-forming lens.

Note that, in all of the embodiments 3 to 5, because the light exiting towards the image side is collimated light, the objective optical system itself forms no image. Therefore, it is used in combination with, for example, an image-forming lens having the lens data shown in Table 4 below and having the lens configuration as shown in FIG. 13. Also herein, because the maximum diameter of the lens can be kept small, namely, 1.8 mm or less (the effective diameter is 1.6 mm or less), for 6.1 mm corresponding to the working distance of the image-forming optical system, it is understood that the small diameter can be maintained for the overall length of the optical system, including the objective optical system and the image-forming optical system (in the above-described embodiment, from 27.63 to 30.53 mm). At this time, observation may be performed by connecting an image fiber to the light receiving surface of a CCD such that they are is positioned at a fourth image plane (image plane). Note that the lens data shown in Table 7 shows an example in which a glass plate for preventing reflection is attached so as to be in contact with the image plane.

TABLE 7

| SURFACE NO. | r | d | nd | vd | EFFECTIVE DIAMETER |
|---|---|---|---|---|---|
| 301 (PUPIL POSITION) |  | 0.67 |  |  |  |
| 302 | 2.96 | 0.47 | 1.487 | 70.2 | 1.6 |
| 303 | ∞ | 0.22 |  |  | 1.6 |
| 304 | ∞ | 0.75 | 1.439 | 94.9 | 1.5 |
| 305 | −1.581 | 0.55 | 1.613 | 44.3 | 1.4 |
| 306 | −6.963 | 0.19 |  |  | 1.3 |
| 307 | 4.4 | 0.47 | 1.613 | 44.3 | 1.3 |
| 308 | 1.717 | 1.05 | 1.439 | 94.9 | 1.2 |
| 309 | −2.634 | 0.1 |  |  | 1 |
| 310 | 1.609 | 0.43 | 1.773 | 49.6 | 0.9 |
| 311 | ∞ | 0.3 | 1.678 | 55.3 | 0.7 |
| 312 | 1.566 | 0.5 |  |  | 0.5 |
| 313 | ∞ | 0.4 | 1.487 | 7.02 | 0.5 |
| IMAGE PLANE | ∞ |  |  |  |  |

Herein, as can be seen from the various embodiments described above, the exit pupil of the objective optical system of the present invention is located at the image side of the lens surface positioned on the extreme image side in the objective optical system. This makes optical combination relatively easy even when the pupil of the image-forming lens is located in the image-forming lens. Thus, in the present invention, by disposing the concave surface of the lens behind a first image, field curvature can be corrected and the tip of the objective optical system can be made even thinner. Furthermore, because the angle of the main beam with respect to the optical axis (the extent of focus) is relaxed and the point at which the main beam and the optical axis intersect can be brought close to the image position, the exit pupil (the pupil position on the image side) can be located outside the lens.

The symbols in the table are as follows:
r: radius of curvature, d: distance between surfaces, nd: refractive index (d line), vd: Abbe number (d line). The unit of length is mm.

Although the present invention has been described above, the following modifications and applications are possible so long as they are within the above-described gist.

(A) The above-described embodiments show the cases where the intermediate image plane is disposed between the fourth lens group $G_4$ and the fifth lens group $G_5$. However, instead of this, the intermediate image plane may be disposed between the lenses constituting the fifth lens group $G_5$. In such a case, the lens, in the fifth lens group $G_5$, whose lens surface closest to the intermediate image plane is a concave surface facing towards the intermediate image plane may be disposed such that the concave surface faces towards the intermediate image plane on the image side.

(B) In vivo observation may be applied not only to so-called microscopes, but also to endoscopes etc., as long as the microscopic optical systems are used to observe a predetermined observation area of a living animal or plant in a magnified state.

(C) Immersion type means an optical system for performing observation in such a manner that the tip portion of the objective optical system is immersed in liquid, such as body fluid or culture fluid, when microscopic observation is performed at a short distance from the living body. The present invention is particularly suited for such an immersion-type optical system.

(D) When the objective optical system is thin and long, because the diameter of the outer cylinder does not increase from the tip portion of the objective optical system towards the image side, it is possible to approach the observation area, while maintaining minimal invasiveness. Thus, this is suitable for any use in which observation is performed at a deep part with a wide field of view, while minimizing damage to the observed object (for example, a living body) or damage in the path leading to the observed object.

(E) It is easy to be used on an observed object whose deep part is intended to be directly observed in a minimally invasive manner without reducing resolution.

(F) The objective optical system of the present invention can be disposed not only in observation means having a tubular exterior, but also in various small optical apparatuses (for example, capsule endoscopes and ultra-small cameras) in which it is preferable that the objective optical system be mounted using a long, thin space.

What is claimed is:

1. An objective optical system comprising, in sequence from an object side: a first group having positive refractive power; a second group having positive refractive power; a third group having negative refractive power; a fourth group having positive refractive power; and a fifth group having positive refractive power, the first group including a plano-convex lens with a convex surface facing towards an image side, the second group including a lens whose extreme-object-side lens surface is a convex surface facing towards the object side, the third group including a lens whose extreme-object-side lens surface is a convex surface facing towards the object side, the fourth group including a lens disposed on the extreme object side, whose image-side lens surface is a convex surface facing towards the image side, and a lens disposed on the extreme image side, whose object-side lens surface is a convex surface facing towards the object side, the fifth group including a combined lens formed by joining a convex lens and a concave lens, a joined surface thereof having negative refractive power, wherein the objective optical system is designed to focus at infinity and has an intermediate image plane between the fourth group and the fifth group.

2. The objective optical system according to claim 1, satisfying the following conditional expression (1):

$$0.15 < F_{12}/(t_{13}*NA) < 0.25 \quad (1)$$

where $F_{12}$: combined focal length of the first and second groups;

$t_{13}$: optical axis length from an object plane to the image side surface of the third group; and NA: object-side numerical aperture of this objective optical system.

3. The objective optical system according to claim 1 or 2, satisfying the following conditional expressions (2) to (5):

$$12 < F_5/F_{12} < 14 \quad (2)$$

$$1.7 < \phi_5/\phi_{12} < 2.5 \quad (3)$$

$$1.75 < n_{12} < 1.90 \quad (4)$$

$$80 < \nu_5 < 95 \quad (5)$$

where $F_{12}$: combined focal length of the first and second groups;

$F_5$: focal length of the fifth group;

$\phi_{12}$: diameter of the smallest lens among the lenses in the first and second groups;

$\phi_5$: diameter of the largest lens among the lenses in the fifth group;

$n_{12}$: largest refractive index (d line) among the lenses in the first and second groups; and $\nu_5$: Abbe number (d line) of the convex lens of the combined lens having the joined surface with negative refractive power in the fifth group.

4. The objective optical system according to claim 1, wherein a lens surface on the extreme object side in the first group is substantially flat, wherein the fifth group includes a lens whose surface closest to the intermediate image plane is a concave surface facing towards the intermediate image plane, and wherein an image-side exit pupil is located at the image side of the lens surface positioned on the extreme image side in the objective optical system.

5. The objective optical system according to claim 4, satisfying the following conditional expression (6):

$$0.28 < (t_5 * R_5)/(Dep*FOV) < 0.55 \quad (6)$$

where $t_5$: distance from the intermediate image plane to the surface closest to the intermediate image plane in the fifth group;

$R_5$: radius of curvature of the surface closest to the intermediate image plane in the fifth group;

Dep: depth of focus on one side at the intermediate image plane, defined by the following expression:

$$Dep = \lambda/(NA/\beta)^2$$

where $\lambda$ is the wavelength of the d line (587.6 nm), $\beta$ is the magnification from an object plane to the intermediate image plane; and FOV: field of view on the object side.

6. The objective optical system according to claim 4, satisfying the following conditional expressions (7) to (11):

$$0.37 < F_{12}/(t_{13}*NA) < 0.45 \quad (7)$$

$$2.0 < \phi_5/\phi_{12} < 2.5 \quad (8)$$

$$1.75 < n_{12} < 1.90 \quad (9)$$

$$0.27 < \Delta n_5 < 0.45 \quad (10)$$

$$30 < \Delta \nu_5 < 55 \quad (11)$$

where $F_{12}$: combined focal length of the first and second groups;

$t_{13}$: optical axis length from an object plane to the image side surface of the third group;

NA: object-side numerical aperture;

$\phi_5$: diameter of the largest lens among the lenses in the fifth group;

$\phi_{12}$: diameter of the smallest lens among the lenses in the first and second groups;

$n_{12}$: largest refractive index (d line) among the lenses in the first and second groups;

$\Delta n_5$: difference in refractive index (d line) of the combined lens having the joined surface with negative refractive power in the fifth group; and $\Delta \nu_5$: difference in Abbe number (d line) of the combined lens having the joined surface with negative refractive power in the fifth group.

7. The objective optical system according to claim 1, comprising an outer cylinder having a substantially uniform diameter that accommodates the first to third groups.

8. The objective optical system according to claim 7, wherein the average inside diameter of the outer cylinder is 1 mm or less.

9. The objective optical system according to claim 7, wherein the dimensional ratio of the outside diameter to length of the outer cylinder is 1:10 or more.

10. The objective optical system according to claim 7, wherein the outer cylinder has an outside diameter of about 1.8 mm or less and a length of about 20 mm or more.

11. The objective optical system according to claim 7, wherein the field of view on the object side is 0.25 or more and the object-side numerical aperture is 0.35 or more.

* * * * *